(12) United States Patent
Matsuura et al.

(10) Patent No.: US 10,973,750 B2
(45) Date of Patent: Apr. 13, 2021

(54) COPOLYMER, THICKENING AGENT CONTAINING SAID COPOLYMER, AND COSMETIC PREPARATION IN WHICH SAID COPOLYMER IS BLENDED

(71) Applicant: FUJIFILM Wako Pure Chemical Corporation, Osaka (JP)

(72) Inventors: Takatoshi Matsuura, Saitama (JP); Yasuyoshi Mori, Saitama (JP); Ayako Kuramoto, Tokyo (JP)

(73) Assignee: FUJIFILM Wako Pure Chemical Corporation, Osaka (JP)

( * ) Notice: Subject to any disclaimer, the term of this patent is extended or adjusted under 35 U.S.C. 154(b) by 0 days.

(21) Appl. No.: 16/089,961

(22) PCT Filed: Mar. 30, 2017

(86) PCT No.: PCT/JP2017/013457
§ 371 (c)(1),
(2) Date: Sep. 28, 2018

(87) PCT Pub. No.: WO2017/170961
PCT Pub. Date: Oct. 5, 2017

(65) Prior Publication Data
US 2019/0110975 A1  Apr. 18, 2019

(30) Foreign Application Priority Data

Mar. 31, 2016 (JP) .............................. JP2016-073296
Oct. 11, 2016 (JP) .............................. JP2016-200446

(51) Int. Cl.
| | |
|---|---|
| *A61K 8/81* | (2006.01) |
| *A61Q 19/00* | (2006.01) |
| *C08F 220/22* | (2006.01) |
| *C08F 220/26* | (2006.01) |
| *C08F 230/02* | (2006.01) |
| *C08F 220/54* | (2006.01) |
| *C09K 3/00* | (2006.01) |
| *C08F 216/14* | (2006.01) |

(Continued)

(52) U.S. Cl.
CPC ............ *A61K 8/8152* (2013.01); *A61K 8/042* (2013.01); *A61K 8/046* (2013.01); *A61K 8/06* (2013.01); *A61K 8/55* (2013.01); *A61Q 1/02* (2013.01); *A61Q 1/10* (2013.01); *A61Q 5/02* (2013.01); *A61Q 5/04* (2013.01); *A61Q 5/06* (2013.01); *A61Q 5/10* (2013.01); *A61Q 15/00* (2013.01); *A61Q 17/04* (2013.01); *A61Q 19/00* (2013.01); *A61Q 19/10* (2013.01); *C08F 216/14* (2013.01); *C08F 220/06* (2013.01); *C08F 220/22* (2013.01); *C08F 220/26* (2013.01); *C08F 220/54* (2013.01); *C08F 230/02* (2013.01); *C08L 33/16* (2013.01); *C09K 3/00* (2013.01); *A61K 2800/10* (2013.01); *A61K 2800/48* (2013.01); *C08F 2800/20* (2013.01)

(58) Field of Classification Search
None
See application file for complete search history.

(56) References Cited

U.S. PATENT DOCUMENTS

| | | | |
|---|---|---|---|
| 4,800,220 A * | 1/1989 | Ribba | .................. C08F 220/06 526/238.23 |
| 5,136,000 A | 8/1992 | Luttenberger et al. | |

(Continued)

FOREIGN PATENT DOCUMENTS

| | | |
|---|---|---|
| JP | 4-255766 | 9/1992 |
| JP | 5-331038 | 12/1993 |

(Continued)

OTHER PUBLICATIONS

Extended European Search Report issued in European Application No. 17775494.2, dated Aug. 30, 2019, 8 pages.

(Continued)

*Primary Examiner* — Melissa L Fisher
(74) *Attorney, Agent, or Firm* — Hamre, Schumann, Mueller & Larson, P.C.

(57) ABSTRACT

An object of the present invention is to provide a copolymer which is capable of forming a viscous aqueous solution having a desired viscosity in the presence of an electrolyte, in particular, a polyvalent electrolyte, a thickening agent comprising the copolymer, and a cosmetic preparation comprising the copolymer. The present invention relates to an acrylic acid ester (A)/compound (B) copolymer, comprising, as constitutional components, an acrylic acid ester (A) and a compound (B), wherein the acrylic acid ester (A) is represented by the general formula [1], and the compound (B) has, in each molecule, a polymerizable unsaturated group and any functional group selected from the group consisting of a carboxyl group, a sulfo group, and a phosphate group, and a weight ratio of the acrylic acid ester (A) and the compound (B), which is (A)/(B), is 9.0/91.0 to 28.5/71.5; a thickening agent comprising the copolymer; and a cosmetic preparation comprising the copolymer;

General Formula [1]:

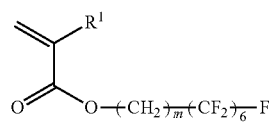

wherein $R^1$ represents a hydrogen atom or an alkyl group having 1 to 6 carbon atoms, and m represents an integer of 2 to 4.

14 Claims, No Drawings

(51) Int. Cl.
*C08L 33/16* (2006.01)
*A61K 8/04* (2006.01)
*A61K 8/06* (2006.01)
*A61K 8/55* (2006.01)
*A61Q 1/02* (2006.01)
*A61Q 1/10* (2006.01)
*A61Q 5/02* (2006.01)
*A61Q 5/04* (2006.01)
*A61Q 5/06* (2006.01)
*A61Q 5/10* (2006.01)
*A61Q 15/00* (2006.01)
*A61Q 17/04* (2006.01)
*A61Q 19/10* (2006.01)
*C08F 220/06* (2006.01)

(56) References Cited

U.S. PATENT DOCUMENTS

| | | | |
|---|---|---|---|
| 6,645,476 B1 | 11/2003 | Morschhauser, et al. | |
| 7,399,478 B2 | 7/2008 | Loffler et al. | |
| 2004/0109835 A1* | 6/2004 | Loffler | A61K 8/86 424/70.12 |
| 2010/0267845 A1 | 10/2010 | Yoshinaka et al. | |
| 2013/0052440 A1* | 2/2013 | Sakamoto | B32B 27/28 428/215 |
| 2017/0040612 A1 | 2/2017 | Komaba et al. | |

FOREIGN PATENT DOCUMENTS

| | | |
|---|---|---|
| JP | 2012-220615 | 11/2012 |
| WO | 2009/084469 | 7/2009 |
| WO | 2015/163302 | 10/2015 |

OTHER PUBLICATIONS

Office Action issued in corresponding European Patent Application No. 17775494.2, Dec. 4, 2020, 6 pages.

* cited by examiner

COPOLYMER, THICKENING AGENT CONTAINING SAID COPOLYMER, AND COSMETIC PREPARATION IN WHICH SAID COPOLYMER IS BLENDED

TECHNICAL FIELD

The present invention relates to a copolymer having thickening properties, a thickening agent containing the copolymer, and a cosmetic preparation in which the copolymer is blended.

BACKGROUND ART

In order to retain active ingredients in the skin and hair and to also improve feeling in use and feeling of high quality, there are some cases where a thickening agent such as a polymer and a surfactant is blended in a cosmetic preparation so that the cosmetic preparation is thickened or is brought into a gelled state. For example, as an organic thickening agent, a natural polymer such as a polysaccharide, casein, and xanthan gum, a semi-natural polymer such as hydroxyethyl cellulose, and a synthetic polymer such as an acrylic polymer, a carboxy vinyl polymer, and polyethylene oxide are used. In addition, as an inorganic thickening agent, a clay mineral such as montmorillonite or silica is used.

Among these thickening agents, a carboxy vinyl polymer is frequently used (for example, Patent Literature 1) since, in addition to being inexpensive, it exhibits a high thickening effect and causes gelling in a small amount. However, in many of the thickening agents, in a case where an electrolyte is added, polymers aggregate, and in a case where an additive amount of the electrolyte exceeds 2% by weight, viscosity is rapidly decreased. Thus, in a case where a high concentration of the electrolyte coexists, there is a problem that viscosity cannot be maintained. In addition, for the carboxy vinyl polymer, there is a problem that it suppresses a decrease in viscosity due to the addition of the electrolyte, but exhibits insufficient effects.

In addition, recently, a (meth)acrylic acid/(meth)acrylic acid alkyl ester copolymer that can be used in the presence of a relatively high concentration of an electrolyte is known (for example, Patent Literature 2). However, due to difficulty of maintaining a sufficient viscosity in the presence of a polyvalent electrolyte such as magnesium and calcium, there is a problem that use of the (meth)acrylic acid/(meth)acrylic acid alkyl ester copolymer is limited.

CITATION LIST

Patent Literature

Patent Literature 1: JP1993-331038 A (JP-H05-331038 A)
Patent Literature 2: WO2009/084469 A

SUMMARY OF INVENTION

Technical Problem

An object of the present invention is to provide a copolymer which is capable of forming a viscous aqueous solution having a desired viscosity in the presence of an electrolyte, in particular, a polyvalent electrolyte, a thickening agent containing the copolymer, and a cosmetic preparation in which the copolymer is blended. As a result of earnest studies on such a copolymer, the present inventors have found that it is possible to provide a copolymer capable of forming a viscous aqueous solution having a desired viscosity by using, as constitutional components of the copolymer, a fluorine-containing acrylic acid ester having a specific structure, and, if necessary, a compound having a polymerizable unsaturated group and a specific acidic group, at a specific ratio, and have completed the present invention.

Solution to Problem

The present invention is constituted as follows.

(1) An acrylic acid ester (A)/compound (B) copolymer, comprising, as constitutional components: an acrylic acid ester (A); and a compound (B), wherein the acrylic acid ester (A) is represented by the general formula [1], and the compound (B) has, in each molecule, a polymerizable unsaturated group and any functional group selected from the group consisting of a carboxyl group, a sulfo group, and a phosphate group, and a weight ratio of the acrylic acid ester (A) and the compound (B), which is (A)/(B), is 9.0/91.0 to 28.5/71.5, General Formula [1]:

wherein $R^1$ represents a hydrogen atom or an alkyl group having 1 to 6 carbon atoms, and m represents an integer of 2 to 4.

(2) A cosmetic preparation comprising the acrylic acid ester (A)/compound (B) copolymer.

(3) A thickening agent comprising the acrylic acid ester (A)/compound (B) copolymer.

Advantageous Effects of Invention

The copolymer of the present invention exerts effects capable of forming a viscous aqueous solution having a desired viscosity in the presence of an electrolyte, in particular, a polyvalent electrolyte. Even in a case where the electrolyte has a high concentration, the copolymer exerts effects capable of maintaining the desired viscosity.

In addition, from the viewpoint that the copolymer of the present invention exerts effects that it has good applying properties, hardly drips, and has a jiggly tactile feeling (elastic tactile feeling), in a case where the copolymer of the present invention is used, it is possible to provide a cosmetic preparation that has excellent feeling in use and applying properties as well as a unique tactile feeling.

Furthermore, from the viewpoint that the copolymer of the present invention exerts effects of excellent transparency, the copolymer of the present invention is suitably used for cosmetic preparations characterized by colorlessness such as a skin lotion or a beauty liquid.

DESCRIPTION OF EMBODIMENTS

The acrylic acid ester (A)/compound (B) copolymer of the present invention includes, as constitutional components, the acrylic acid ester (A) and the compound (B), wherein the acrylic acid ester (A) is represented by the general formula [1], and the compound (B) has, in each molecule, a polymerizable unsaturated group and any functional group selected from the group consisting of a carboxyl group, a sulfo group, and a phosphate group, and a ratio (weight ratio) of the acrylic acid ester (A) and the compound (B), which is (A)/(B), is 9.0/91.0 to 28.5/71.5, General Formula [1]:

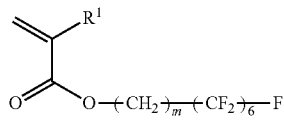

[1]

wherein $R^1$ represents a hydrogen atom or an alkyl group having 1 to 6 carbon atoms, and m represents an integer of 2 to 4.

In the present invention, the "acrylic acid ester (A)/compound (B) copolymer" means a copolymer having a constitutional unit derived from an acrylic acid ester (A) and a constitutional unit derived from a compound (B), which contains, as constitutional components, at least the acrylic acid ester (A) and the compound (B).

As an alkyl group having 1 to 6 carbon atoms represented by $R^1$ in the general formula [1], an alkyl group having 1 to 3 carbon atoms is preferable, and, among these, an alkyl group having 1 carbon atom is more preferable. In addition, the alkyl group may be any of linear, branched, or cyclic. Specific examples of such an alkyl group include a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, and a cyclohexyl group. Among these, for example, a linear, branched, or cyclic alkyl group having 1 to 3 carbon atoms such as a methyl group, an ethyl group, an n-propyl group, an isopropyl group, and a cyclopropyl group is preferable, among which a methyl group which is an alkyl group having 1 carbon atom is more preferable.

As $R^1$ in the general formula [1], a hydrogen atom is more preferable.

In the general formula [1], m is an integer of 2 to 4. Among these, an integer of 2 to 3 is preferable, among which 2 is more preferable.

Specific examples of the (A) acrylic acid ester represented by the general formula [1] include 2-perfluorohexylethyl (meth)acrylate, 3-perfluorohexylpropyl (meth)acrylate, and 4-perfluorohexylbutyl (meth)acrylate.

In the specific examples, (meth)acrylate means acrylate and/or methacrylate.

Among the specific examples of the (A) acrylic acid ester represented by the general formula [1], 2-perfluorohexylethyl (meth)acrylate is preferable, and, among these, 2-perfluorohexylethyl acrylate is particularly preferable.

It should be noted that as the (A) acrylic acid ester represented by the general formula [1], a commercially available one may be used, or one appropriately synthesized by a method known per se may be used.

The compound (B) having a polymerizable unsaturated group and any functional group selected from the group consisting of a carboxyl group, a sulfo group, and a phosphate group in each molecule is, for example, a compound that has a polymerizable unsaturated group such as a carbon-carbon double bond and a carbon-carbon triple bond, and any functional group selected from the group consisting of a carboxyl group, a sulfo group, and a phosphate group in each molecule, in which the polymerizable unsaturated group reacts with (A) the acrylic acid ester represented by the general formula [1] to form the acrylic acid ester (A)/compound (B) copolymer.

Specific examples of such a compound (B) include those represented by the general formulae [2] to [5], General Formula [2]:

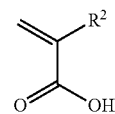

[2]

wherein $R^2$ represents a hydrogen atom or an alkyl group having 1 to 6 carbon atoms, General Formula [3]:

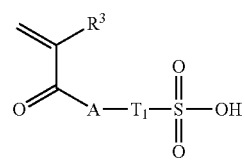

[3]

wherein A represents an oxygen atom or an —NH— group, $T_1$ represents an alkylene group having 1 to 6 carbon atoms which may have a hydroxy group, and $R^3$ represents a hydrogen atom or an alkyl group having 1 to 6 carbon atoms, General Formula [4]:

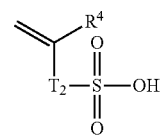

[4]

wherein $T_2$ represents a bond or an alkylene group having 1 to 6 carbon atoms, and $R^4$ represents a hydrogen atom or an alkyl group having 1 to 6 carbon atoms, General Formula [5]:

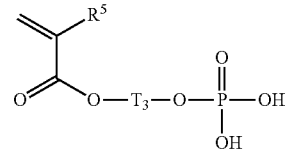

[5]

wherein $T_3$ represents an alkylene group having 1 to 6 carbon atoms, and $R^5$ represents a hydrogen atom or an alkyl group having 1 to 6 carbon atoms.

As an alkyl group having 1 to 6 carbon atoms represented by $R^2$ to $R^5$ in the general formulae [2] to [5], an alkyl group having 1 to 3 carbon atoms is preferable, and, among these, an alkyl group having 1 carbon atom is more preferable. In addition, the alkyl group may be any of linear, branched, or cyclic. Specific examples of such an alkyl group include a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, an isopentyl group, a sec-pentyl group, a tert-pentyl group, an neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, and a cyclohexyl group. Among these, for example, a linear, branched, or cyclic alkyl group having 1 to 3 carbon atoms such as a methyl group, an ethyl group, an n-propyl group, an isopropyl group, and a cyclopropyl group is preferable, among which a methyl group which is an alkyl group having 1 carbon atom is more preferable.

As $R^2$ to $R^5$ in the general formulae [2] to [5], a hydrogen atom is more preferable.

As A in the general formula [3], an oxygen atom is more preferable.

As an alkylene group having 1 to 6 carbon atoms which may have a hydroxy group, represented by $T_1$ in the general formula [3], an alkylene group having 1 to 4 carbon atoms which may have a hydroxy group is preferable, and, among these, an alkylene group having 2 to 4 carbon atoms which may have a hydroxy group is more preferable. The alkylene group may be either linear or branched, and, in a case where the alkylene group has a hydroxy group, a number of the hydroxy group may be one or plural. Specific examples of such an alkylene group include a methylene group, a hydroxymethylene group, a dimethylene group (an ethylene group), a hydroxydimethylene group (a hydroxyethylene group), a trimethylene group, a 1-hydroxytrimethylene group, a 2-hydroxytrimethylene group, an isopropylene group, a hydroxyisopropylene group, a tetramethylene group, a hydroxytetramethylene group, a 1-methyltrimethylene group, a 2-methyltrimethylene group, 1,1-dimethyldimethylene group, a pentamethylene group, and a hexamethylene group. Among these, a dimethylene group (an ethylene group), a trimethylene group, a 2-hydroxytrimethylene group, and a 1,1-dimethyldimethylene group are preferable.

The bond represented by $T_2$ in the general formula [4] means that there is no atom in $T_2$, and the "sulfur atom" bonded to $T_2$ and the "carbon atom bonded to $R^{4}$" which is bonded to $T_2$ are directly bonded to each other without $T_2$.

As an alkylene group having 1 to 6 carbon atoms represented by $T_2$ in the general formula [4], an alkylene group having 1 carbon atom is preferable. In addition, the alkylene group may be either linear or branched. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, and a hexamethylene group, and, among these, a methylene group which is an alkylene group having 1 carbon atom is preferable.

As an alkylene group having 1 to 6 carbon atoms represented by $T_3$ in the general formula [5], an alkylene group having 2 carbon atoms is preferable. In addition, the alkylene group may be either linear or branched. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, and a hexamethylene group, and, among these, a dimethylene group (an ethylene group) which is an alkylene group having 2 carbon atoms is preferable.

Specific examples of a compound represented by the general formula [2] include acrylic acid and methacrylic acid.

Specific examples of a compound represented by the general formula [3] include 2-(acryloyloxy)ethanesulfonic acid, 2-(methacryloyloxy)ethanesulfonic acid, 3-(acryloyloxy)propanesulfonic acid, 3-(methacryloyloxy)propanesulfonic acid, 2-acryloyloxy-2-methylpropanesulfonic acid, 2-methacryloyloxy-2-methylpropanesulfonic acid, 3-acryloyloxy-2-hydroxypropanesulfonic acid, 3-methacryloyloxy-2-hydroxypropanesulfonic acid, 2-acrylamido-2-methylpropanesulfonic acid, and 2-methacrylamido-2-methylpropanesulfonic acid.

Specific examples of a compound represented by the general formula [4] include vinylsulfonic acid and allylsulfonic acid.

Specific examples of a compound represented by the general formula [5] include 2-(acryloyloxy)ethyl phosphate and 2-(methacryloyloxy)ethyl phosphate.

As a compound (B), a compound represented by the general formula [2] is more preferable. Among these, an acrylic acid and a methacrylic acid are more preferable, among which an acrylic acid is particularly preferable.

As a compound (B), a commercially available one may be used, or one appropriately synthesized by a method known per se may be used.

The ratio (weight ratio) of the acrylic acid ester (A) and the compound (B), which is (A)/(B), in the copolymer of the present invention is usually 9.0/91.0 to 28.5/71.5, preferably 14.0/86.0 to 27.3/72.7, more preferably 14.0/86.0 to 25.0/75.0, and even more preferably 14.5/85.5 to 20.0/80.0. In a case where the ratio (weight ratio) of the acrylic acid ester (A) and the compound (B) is smaller than 9.0/91.0, at the time of preparing a viscous aqueous solution, sufficient viscosity is not obtained in the presence of an electrolyte, which makes it difficult to use the solution. In addition, in a case where the ratio (weight ratio) of the acrylic acid ester (A) and the compound (B) exceeds 28.5/71.5, at the time of preparing a viscous aqueous solution, not only does viscosity become extremely high in the presence of a low concentration of an electrolyte, but as a concentration of an electrolyte increases, viscosity rapidly decreases, and viscosity changes greatly depending on a concentration of an electrolyte, which makes it difficult to use the solution.

In a case where the ratio (weight ratio) of the acrylic acid ester (A) and the compound (B), which is (A)/(B), in the copolymer of the present invention falls within a range of 14.0/86.0 to 25.0/75.0, at the time of preparing a viscous aqueous solution, it is easy to maintain a high viscosity in the presence of a high concentration of an electrolyte. Thus, the copolymer of the present invention in which the acrylic acid ester (A) and the compound (B) falls within the range of the ratio (weight ratio) can be suitably used for cosmetic preparation in which a high concentration of an electrolyte coexists.

In a case where the ratio (weight ratio) of the acrylic acid ester (A) and the compound (B), which is (A)/(B), in the copolymer of the present invention falls within a range of 14.5/85.5 to 20.0/80.0, at the time of preparing a viscous aqueous solution, it is easy to maintain very high viscosity in the presence of a high concentration of an electrolyte.

Thus, the copolymer of the present invention in which the acrylic acid ester (A) and the compound (B) falls within the range of the ratio (weight ratio) can be suitably used for cosmetic preparation characterized by a high viscosity.

The ratio (molar ratio) of the acrylic acid ester (A) and the compound (B), which is (A)/(B), in the copolymer of the present invention is usually 1.5/98.5 to 6.5/93.5, preferably 2.0/98.0 to 6.0/94.0, more preferably 2.5/97.5 to 5.5/94.5, even more preferably 2.5/97.5 to 4.5/95.5, and still more preferably 3.0/97.0 to 4.0/96.0. In a case where the ratio (molar ratio) of the acrylic acid ester (A) and the compound (B) is smaller than 1.5/98.5, at the time of preparing a viscous aqueous solution, sufficient viscosity is not obtained in the presence of an electrolyte, which makes it difficult to use the solution. In addition, in a case where the ratio (molar ratio) of the acrylic acid ester (A) and the compound (B) exceeds 6.5/93.5, at the time of preparing a viscous aqueous solution, not only does viscosity become extremely high in the presence of a low concentration of an electrolyte, but as a concentration of an electrolyte increases, viscosity rapidly decreases, and viscosity changes greatly depending on a concentration of an electrolyte, which makes it difficult to use the solution.

In a case where the ratio (molar ratio) of the acrylic acid ester (A) and the compound (B), which is (A)/(B), in the copolymer of the present invention falls within a range of 2.5/97.5 to 4.5/95.5, at the time of preparing a viscous aqueous solution, it is easy to maintain a high viscosity in the presence of a high concentration of an electrolyte. Thus, the copolymer of the present invention in which the acrylic acid ester (A) and the compound (B) falls within the range of the ratio (molar ratio) can be suitably used for cosmetic preparation in which a high concentration of an electrolyte coexists.

In a case where the ratio (molar ratio) of the acrylic acid ester (A) and the compound (B), which is (A)/(B), in the copolymer of the present invention falls within a range of 3.0/97.0 to 4.0/96.0, at the time of preparing a viscous aqueous solution, it is easy to maintain very high viscosity in the presence of a high concentration of an electrolyte. Thus, the copolymer of the present invention in which the acrylic acid ester (A) and the compound (B) falls within the range of the ratio (molar ratio) can be suitably used for cosmetic preparation characterized by a high viscosity.

The acrylic acid ester (A)/compound (B) copolymer of the present invention may further contain, as a constitutional component, a compound (C) having two or more ethylenically unsaturated groups. That is, the copolymer of the present invention which further contains a compound (C) is a copolymer having a constitutional unit derived from an acrylic acid ester (A), a constitutional unit derived from a compound (B), and a constitutional unit derived from a compound (C), which contains, as constitutional components, at least the acrylic acid ester (A), the compound (B), and the compound (C).

The copolymer of the present invention is preferably acrylic acid ester (A)/compound (B)/compound (C) copolymer which further contains, as a constitutional component, the compound (C) having two or more ethylenically unsaturated groups.

The compound (C) having two or more ethylenically unsaturated groups is a compound that has two or more ethylenically unsaturated groups in each molecule which can react with an acrylic acid ester (A) and a compound (B), and that plays a role of a so-called crosslinking agent.

Specific examples of such a compound (C) include those represented by the general formulae [6] to [16], General Formula [6]:

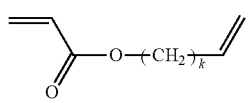

wherein k represents an integer of 1 to 6,

General Formula [7]:

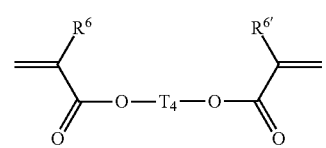

wherein $T_4$ represents an alkylene group having 1 to 20 carbon atoms, a group represented by the general formula [7-1], or a group represented by the general formula [7-2], and $R^6$ and $R^{6'}$ each independently represent a hydrogen atom or a methyl group, General Formula [7-1]:

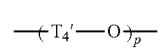

wherein p pieces of $T_4'$ each independently represent an alkylene group having 1 to 6 carbon atoms, and p represents an integer of 1 to 6, General Formula [7-2]:

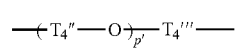

wherein p' pieces of $T_4''$ and $T_4'''$ each independently represent an alkylene group having 1 to 6 carbon atoms, and p' represents an integer of 1 to 12, General Formula [8]:

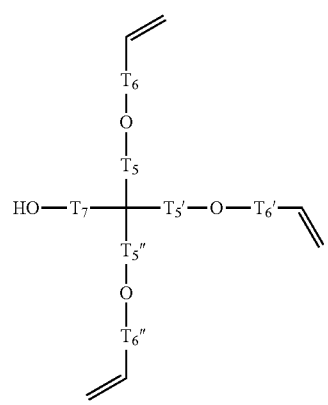

wherein $T_5$, $T_5'$, $T_5''$, $T_6'$, $T_6''$, and $T_7$ each independently represent an alkylene group having 1 to 3 carbon atoms, General Formula [9]:

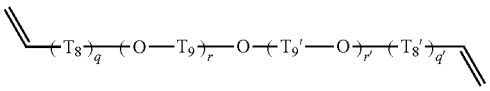

wherein q pieces of $T_8$, q' pieces of $T_8'$, r pieces of $T_9$, and r' pieces of $T_9'$ each independently represent an alkylene group having 1 to 6 carbon atoms, q and q' represent 0 or 1, r represents an integer of 1 to 6, and r' represents an integer of 0 to 6, General Formula [10]:

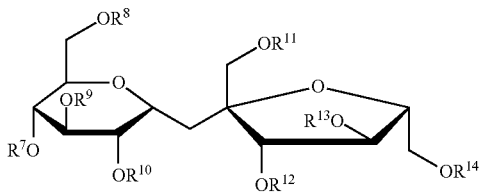

wherein $R^7$ to $R^{14}$ each independently represent a hydrogen atom, a vinyl group, or a vinylcarbonyl group, where at least two of $R^7$ to $R^{14}$ each represent a vinyl group or a vinylcarbonyl group, General Formula [11]:

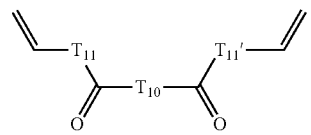

wherein $T_{10}$, $T_{11}$, and $T_{11}'$ each independently represent an alkylene group having 1 to 6 carbon atoms, General Formula [12]:

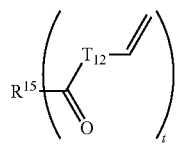

wherein t pieces of $T_{12}$ each independently represents an alkylene group having 1 to 6 carbon atoms, $R^{15}$ represents a divalent to tetravalent aromatic hydrocarbon group having 6 to 10 carbon atoms, and t represents an integer of 2 to 4, General Formula [13]:

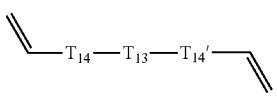

wherein $T_{13}$ represents an alkylene group having 1 to 6 carbon atoms, and $T_{14}$ and $T_{14}'$ each independently represent an arylene group having 6 to 10 carbon atoms, General Formula [14]:

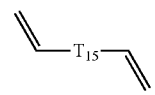

wherein $T_{15}$ represents an arylene group having 6 to 10 carbon atoms,

General Formula [15]:

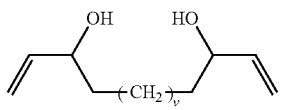

wherein v represents an integer of 0 to 6,

General Formula [16]:

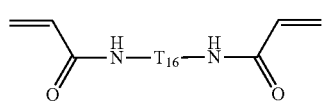

wherein $T_{16}$ represents an alkylene group having 1 to 6 carbon atoms.

In the general formula [6], k is more preferably an integer of 1 to 4, and, among these, 1 is even more preferable.

As $R^6$ and $R^{6'}$ in the general formula [7], a hydrogen atom is more preferable.

As an alkylene group having 1 to 20 carbon atoms represented by $T_4$ in the general formula [7], an alkylene group having 1 to 10 carbon atoms is preferable. In addition, the alkylene group may be any of linear, branched, or cyclic, and, among these, the linear one is preferable. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, a cyclohexylene group, a heptamethylene group, a cycloheptylene group, an octamethylene group, a cyclooctylene group, a nonamethylene group, a cyclononylene group, a decamethylene group, a cyclodecylene group, an undecamethylene group, a cycloundecylene group, a dodecamethylene group, a cyclododecylene group, a tridecamethylene group, a cyclotridecylene group, a tetradecamethylene group, a cyclotetradecylene group, a pentadecamethylene group, a cyclopentadecylene group, a hexadecamethylene group, a cyclohexadecylene group, a heptadecamethylene group, a cycloheptadecylene group, an octadecamethylene group, a cyclooctadecylene group, a nonadecamethylene group, a cyclononadecylene group, an icosylene group, and a cycloicosylene group. Among these, a linear alkylene group having 1 to 20 carbon atoms such as a methylene group, a dimethylene group (an ethylene group), a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an octadecamethylene group, a nonadecamethylene group, and an icosylene group is preferable, among which a linear alkyl group having 1 to 10 carbon atoms such as a methylene group, a dimethylene group (an ethylene group), a trimethylene group, a tetramethylene group, a pentamethylene group, a hexamethylene group, a heptamethylene group, an octamethylene group, a nonamethylene group, and a decamethylene group is more preferable.

As an alkylene group having 1 to 6 carbon atoms represented by $T_4'$ in the general formula [7-1], and $T_4''$ and $T_4'''$ in the general formula [7-2], an alkylene group having 1 to 3 carbon atoms is preferable. In addition, the alkylene group may be any of linear, branched, or cyclic, and, among these, the linear one is preferable. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, and a cyclohexylene group, and, among these, a linear alkylene group having 1 to 3 carbon atoms such as a methylene group, a dimethylene group (an ethylene group), and a trimethylene group is preferable.

In the general formula [7-1], p is more preferably an integer of 2 to 6, and, among these, an integer of 4 to 6 is even more preferable.

In the general formula [7-2], p' is more preferably an integer of 1 to 7. Among these, an integer of 1 to 5 is more preferable, among which an integer of 1 to 3 is particularly preferable.

As an alkylene group having 1 to 3 carbon atoms represented by $T_5$, $T_5'$, $T_5''$, $T_6$, $T_6'$, $T_6''$, and $T_7$ in the general formula [8], an alkylene group having 1 carbon atom is preferable. In addition, the alkylene group may be either linear or branched. Specific examples of such an alkylene group include a methylene group, a dimethylene group (an ethylene group), a trimethylene group, and an isopropylene group, and, among these, a methylene group which is an alkylene group having 1 carbon atom is preferable.

As an alkylene group having 1 to 6 carbon atoms represented by $T_8$, $T_8'$, $T_9$, and $T_9'$ in the general formula [9], an alkylene group having 1 to 3 carbon atoms is preferable, and, among these, an alkylene group having 1 carbon atom is more preferable. In addition, the alkylene group may be any of linear, branched, or cyclic, and, among these, the linear one is preferable. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, and a cyclohexylene group. Among these, in $T_8$ and $T_8'$, a methylene group which is an alkylene group having 1 carbon atom is preferable, and, in $T_9$ and $T_9'$, a linear alkylene group having 1 to 3 carbon atoms such as a methylene group, a dimethylene group (an ethylene group), and a trimethylene group is preferable.

In the general formula [9], q and q' is more preferably 1.

In the general formula [9], r is more preferably an integer of 1 to 2.

In the general formula [9], r' is more preferably an integer of 0 to 2.

It is sufficient that at least two of $R^7$ to $R^{14}$ in the general formula [10] are each a vinyl group or a vinylcarbonyl group. Among these, it is preferable that 5 to 8 thereof are each a vinyl group or a vinylcarbonyl group, among which it is more preferable that 5 to 7 thereof are each a vinyl group or a vinylcarbonyl group.

An alkylene group having 1 to 6 carbon atoms represented by $T_{10}$, $T_{11}$, and $T_{11}'$ in the general formula [11] may be any of linear, branched, or cyclic. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, and a cyclohexylene group. Among these, in $T_{10}$, a cyclopentylene group and a cyclohexylene group are preferable, among which a cyclohexylene group is more preferable. In $T_{11}$ and $T_{11}'$, a methylene group and a dimethylene group (an ethylene group) are preferable, among which a methylene group is more preferable.

Examples of a divalent to tetravalent aromatic hydrocarbon group having 6 to 10 carbon atoms represented by $R^{15}$ in the general formula [12] include a divalent aromatic hydrocarbon group having 6 to 10 carbon atoms (an arylene group) such as a phenylene group and a naphthylene group, a trivalent aromatic hydrocarbon group derived from benzene and naphthalene, and a tetravalent aromatic hydrocarbon group derived from benzene and naphthalene. Among these, a trivalent to tetravalent aromatic hydrocarbon group having 6 carbon atoms is preferable.

As an alkylene group having 1 to 6 carbon atoms represented by $T_{12}$ in the general formula [12], an alkylene group having 1 to 3 carbon atoms is preferable. In addition, the alkylene group may be any of linear, branched, or cyclic, and, among these, the linear one is preferable. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, and a cyclohexylene group, and, among these, a linear alkylene group having 1 to 3 carbon atoms such as a methylene group, a dimethylene group (an ethylene group), and a trimethylene group is preferable.

In the general formula [12], t is more preferably an integer of 3 to 4.

As an alkylene group having 1 to 6 carbon atoms represented by $T_{13}$ in the general formula [13], an alkylene group having 1 to 3 carbon atoms is preferable. In addition, the alkylene group may be any of linear, branched, or cyclic, and, among these, the linear one is preferable. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, and a cyclohexylene group, and, among these, a linear alkylene group having 1 to 3 carbon atoms such as a methylene group, a dimethylene group (an ethylene group), and a trimethylene group is preferable.

Examples of such an arylene group having 6 to 10 carbon atoms represented by $T_{14}$ and $T_{14}'$ in the general formula

[13] include an arylene group having 6 carbon atoms such as a phenylene group, and an arylene group having 10 carbon atoms such as a naphthylene group, and, among these, a phenylene group which is an arylene group having 6 carbon atoms is preferable.

Examples of such an arylene group having 6 to 10 carbon atoms represented by $T_{15}$ in the general formula [14] include an arylene group having 6 carbon atoms such as a phenylene group, and an arylene group having 10 carbon atoms such as a naphthylene group, and among these, a phenylene group which is an arylene group having 6 carbon atoms is preferable.

In the general formula [15], v is more preferably an integer of 0 to 2, and, among these, 0 is even more preferable.

As an alkylene group having 1 to 6 carbon atoms represented by $T_{16}$ in the general formula [16], an alkylene group having 1 to 3 carbon atoms is preferable, and, among these, an alkylene group having 1 carbon atom is more preferable. In addition, the alkylene group may be any of linear, branched, or cyclic, and, among these, the linear one is preferable. Specific examples of such an alkylene group include a methylene group, a dimethylene group (an ethylene group), a trimethylene group, an isopropylene group, a tetramethylene group, a 1-methyltrimethylene group, a 2-methyltrimethylene group, a 1,1-dimethyldimethylene group, a pentamethylene group, a cyclopentylene group, a hexamethylene group, and a cyclohexylene group. Among these, a linear alkylene group having 1 to 3 carbon atoms such as a methylene group, a dimethylene group (an ethylene group), and a trimethylene group is preferable, among which a methylene group is more preferable.

As a compound (C), a compound represented by the general formula [7], a compound represented by the general formula [8], a compound represented by the general formula [9], and a compound represented by the general formula [16] are preferable.

Specific examples of a compound represented by the general formula [7] include 1,10-decanediol diacrylate.

Specific examples of a compound represented by the general formula [8] include pentaerythritol triallyl ether.

Specific examples of a compound represented by the general formula [9] include dialkylene glycol diallyl ether such as diethylene glycol diallyl ether, dipropylene glycol diallyl ether, and dibutylene glycol diallyl ether, and polyalkylene glycol diallyl ether such as polyethylene glycol diallyl ether, polypropylene glycol diallyl ether, and polybutylene glycol diallyl ether.

Specific examples of a compound represented by the general formula [16] include N,N'-methylenebisacrylamide.

Among the compound represented by the general formula [7], the compound represented by the general formula [8], the compound represented by the general formula [9] and the compound represented by the general formula [16], 1,10-decanediol diacrylate, pentaerythritol triallyl ether, diethylene glycol diallyl ether, and N,N'-methylenebisacrylamide are preferable, among which diethylene glycol diallyl ether is more preferable.

As a compound (C), a commercially available one may be used, or one appropriately synthesized by a method known per se may be used.

The proportion of the compound (C) in the copolymer of the present invention is usually 0.0001 to 1.5 parts by weight, with respect to a total of the acrylic acid ester (A) and the compound (B) which is 100 parts by weight, preferably 0.02 to 1.5 parts by weight, more preferably 0.04 to 1.25 parts by weight, even more preferably 0.05 to 1.01 parts by weight, and particularly preferably 0.20 to 0.35 parts by weight. In a case where a total of the acrylic acid ester (A) and the compound (B) is set to be 100 parts by weight, and an amount used of the compound (C) exceeds 1.5 parts by weight with respect to the 100 parts by weight, at the time of preparing a viscous aqueous solution, sufficient viscosity is not obtained in the presence of an electrolyte, which makes it difficult to use the solution.

In a case where the proportion of the compound (C) in the copolymer of the present invention falls within the range of 0.05 to 1.01 parts by weight, at the time of preparing a viscous aqueous solution, it is easy to maintain a high viscosity in the presence of a high concentration of an electrolyte. Thus, the copolymer of the present invention in which the proportion of the compound (C) falls within the parts by weight range can be suitably used for cosmetic preparation in which a high concentration of an electrolyte coexists.

In a case where the proportion of the compound (C) in the copolymer of the present invention falls within the range of 0.20 to 0.35 parts by weight, at the time of preparing a viscous aqueous solution, it is easy to maintain very high viscosity in the presence of a high concentration of an electrolyte. Thus, the copolymer of the present invention in which the proportion of the compound (C) falls within the parts by weight range can be suitably used for cosmetic preparation characterized by a high viscosity.

The proportion of the compound (C) in the copolymer of the present invention is usually 0.00005 to 1.0 mol, with respect to a total of the acrylic acid ester (A) and the compound (B) which is 100 mol, preferably 0.0005 to 0.70 mol, more preferably 0.0005 to 0.60 mol, even more preferably 0.0005 to 0.50 mol, and particularly preferably 0.07 to 0.14 mol. In a case where a total of the acrylic acid ester (A) and the compound (B) is set to be 100 mol, and an amount used of the compound (C) exceeds 1.0 mol with respect to the 100 mol, at the time of preparing a viscous aqueous solution, sufficient viscosity is not obtained in the presence of an electrolyte, which makes it difficult to use the solution.

In the copolymer of the present invention, in particular, in a case where a ratio (molar ratio) of the acrylic acid ester (A) and the compound (B), which is (A)/(B), is preferably 2.5/97.5 to 3.5/96.5, and more preferably 3.0/97.0, the proportion of the compound (C) is preferably 0.01 to 1.0 mol, with respect to a total of the acrylic acid ester (A) and the compound (B) which is 100 mol, more preferably 0.03 to 0.70 mol, even more preferably 0.05 to 0.60 mol, particularly preferably 0.07 to 0.50 mol, and most preferably 0.07 to 0.14 mol.

In the copolymer of the present invention, in particular, in a case where a ratio (molar ratio) of the acrylic acid ester (A) and the compound (B), which is (A)/(B), is preferably 4.5/95.5 to 5.5/94.5, and more preferably 5.0/95.0, the proportion of the compound (C) is preferably 0.00005 to 0.70 mol, with respect to a total of the acrylic acid ester (A) and the compound (B) which is 100 mol, more preferably 0.0005 to 0.70 mol, even more preferably 0.0005 to 0.50 mol, particularly preferably 0.0005 to 0.40 mol, and most preferably 0.0005 to 0.14 mol.

In the copolymer of the present invention, in a case where the ratio (molar ratio) of the acrylic acid ester (A) and the compound (B), which is (A)/(B), is 4.5/95.5 to 5.5/94.5, in particular, 5.0/95.0, a copolymer containing no compound (C) may be desirable in some cases.

The copolymer of the present invention may further contain a compound (D) as a constitutional component other than the acrylic acid ester (A), the compound (B), and the compound (C).

Examples of such a compound (D) include (meth)acrylic acid ester such as methyl (meth)acrylate, ethyl (meth)acrylate, and butyl (meth)acrylate. It should be noted that, as a compound (D), a commercially available one may be used, or one appropriately synthesized by a method known per se may be used.

The copolymer of the present invention preferably includes an acrylic acid ester (A), a compound (B), and a compound (C) without containing a compound (D).

A method for producing the copolymer of the present invention is not particularly limited, and examples thereof include the following method.

(A) an acrylic acid ester represented by the general formula [1], (B) a compound having, in each molecule, a polymerizable unsaturated group and any functional group selected from the group consisting of a carboxyl group, a sulfo group, and a phosphate group, a compound (C) having two or more ethylenically unsaturated groups, and, if necessary, a compound (D) are stirred in a solvent under an inert gas atmosphere, and polymerized using a polymerization initiator, so that the copolymer of the present invention can be produced.

Examples of an inert gas for obtaining the inert gas atmosphere include nitrogen gas and argon gas.

The solvent is not particularly limited as long as it does not react with the acrylic acid ester (A), the compound (B), the compound (C) and, if necessary, the compound (D), and does not inhibit polymerization reactions thereof. Specific examples of such a solvent include purified water such as distilled water and deionized water, for example, water such as ultrapure water; an aliphatic hydrocarbon-based solvent such as n-hexane, cyclohexane, n-heptane, n-octane, and isooctane; a halogenated aliphatic hydrocarbon-based solvent such as dichloromethane, trichloromethane (chloroform), and tetrachloromethane (carbon tetrachloride); an aromatic hydrocarbon-based solvent such as benzene, toluene, and xylene; an ether-based solvent such as diethyl ether, diisopropyl ether, methyl-tert-butyl ether, cyclopentyl methyl ether, tetrahydrofuran, 2-methyl tetrahydrofuran, and 1,4-dioxane; a glycol ether-based solvent such as ethylene glycol dimethyl ether, propylene glycol dimethyl ether, ethylene glycol diethyl ether, propylene glycol diethyl ether, diethylene glycol dimethyl ether, dipropylene glycol dimethyl ether, and dipropylene glycol diethyl ether; a glycol ether acetate-based solvent such as ethylene glycol monoethyl ether acetate, diethylene glycol monoethyl ether acetate, diethylene glycol monobutyl ether acetate, propylene glycol monomethyl ether acetate, propylene glycol monoethyl ether acetate, dipropylene glycol monomethyl ether acetate, and dipropylene glycol monoethyl ether acetate; a ketone-based solvent such as 2-propanone (acetone), 2-butanone (ethyl methyl ketone), and 4-methyl-2-pentanone (methyl isobutyl ketone); an ester-based solvent such as ethyl acetate, n-propyl acetate, isopropyl acetate, isobutyl acetate, sec-butyl acetate, tert-butyl acetate, ethyl butyrate, and isoamyl butyrate; an amide-based solvent such as N,N-dimethylformam ide, N,N-dimethylacetam ide, 1-methyl-2-pyrrolidinone (N-methylpyrrolidone), and 1,3-dimethyl-2-imidazolidinone (dimethylethyleneurea). It should be noted that one of solvents may be used alone, or two or more thereof may be used in combination. In addition, as a solvent, a commercially available one may be used.

An amount used of the solvent is usually 100 to 5,000 parts by weight with respect to 100 parts by weight of the compound (B), and preferably 300 to 3,000 parts by weight, from the viewpoint of practicality and economics.

The polymerization initiator is not particularly limited as long as it is a polymerization initiator used in this field. Specific examples of such a polymerization initiator include radical polymerization initiators, for example, persulfates such as persulfuric acid, sodium persulfate, potassium persulfate, and ammonium persulfate; hydroperoxides such as hydrogen peroxide and tert-butyl hydroperoxide; peroxydicarbonates such as di(4-tert-butylcyclohexyl)peroxydicarbonate; and azo-based compounds such as 2,2'-azobis(2-methylpropionitrile), 2,2'-azobis(2-methylbutyronitrile), 2,2'-azobis(2,4-dimethylvaleronitrile), and 2,2'-azobis(N-butyl-2-methylpropionamide). It should be noted that, as a polymerization initiator, a commercially available one may be used, or one appropriately synthesized by a method known per se may be used.

An amount used of the polymerization initiator is usually 0.0001 to 0.002 mol with respect to 1 mol of the compound (B), and preferably 0.0002 to 0.001 mol. In a case where an amount used of the polymerization initiator is too small, a reaction rate becomes slow. Thus, it may not be economical, and a polymerization reaction may not proceed. In addition, in a case where an amount used of the polymerization initiator is too large, a polymerization reaction may proceed rapidly, which makes it difficult to control the reaction.

It is desirable that polymerization in a case of producing the copolymer of the present invention is carried out under a heating condition and/or a light (an active energy ray) irradiation condition.

A reaction temperature in a case where the polymerization is carried out under a heating condition is usually 40° C. to 120° C., preferably 45° C. to 100° C., and more preferably 50° C. to 90° C. In a case where a reaction temperature is lower than 40° C., a viscosity of a reaction solution may increase, which makes it difficult to perform a uniform stirring. In addition, in a case where a reaction temperature exceeds 120° C., a reaction may proceed rapidly, which makes it difficult to control the reaction. A reaction time varies depending on a reaction temperature. Thus, although a reaction time cannot be described unconditionally, it is usually 0.5 to 6 hours.

A wavelength of light (an active energy ray) in a case where the polymerization is carried out under a light (an active energy ray) irradiation condition is not particularly limited as long as a polymerization reaction to proceed well. A specific example of a wavelength of light (an active energy ray) is usually 1 to 1,000 nm, and examples of the light having such a wavelength include X-ray, ultraviolet ray, visible light, and infrared ray. An irradiation amount (an accumulated exposure amount) of light (an active energy ray) is not particularly limited as long as a polymerization reaction proceeds well. A specific example of the irradiation amount (the accumulated exposure amount) of light (an active energy ray) is usually 0.1 J or more, preferably 0.5 J or more, and more preferably 1.0 J or more. In addition, a reaction temperature in a case where the polymerization is carried out under a light (an active energy ray) irradiation condition may be appropriately set. A reaction time varies depending on a wavelength of light (an active energy ray) and an irradiation amount (an accumulated exposure amount). Thus, although a reaction time cannot be described unconditionally, it is usually 0.5 to 6 hours.

A post-treatment method and a purification method used in a case of producing the copolymer of the present invention may be a general method which is usually carried out in this field. For example, a method in which, after polymerization is terminated, if necessary, a reaction solution is cooled, a copolymer precipitated in the solution is obtained by filtration, and the copolymer obtained by filtration is dried, or the like is adopted, so that the copolymer of the present invention can be obtained. In addition, if necessary, the copolymer obtained by filtration is added to an appropriate precipitation agent, so that the copolymer may be purified.

The acrylic acid ester (A)/compound (B) copolymer of the present invention thus obtained, which has the following characteristic (1), is useful.

(1) an aqueous solution containing 1% by weight of the acrylic acid ester (A)/compound (B) copolymer and 3% by weight of ascorbyl magnesium phosphate, and having a pH of 8 has a viscosity of 5,000 mPa·s or more at 20° C.

That is, acrylic acid ester (A)/compound (B) copolymer is obtained by using each of (A) an acrylic acid ester represented by the general formula [1], and (B) a compound having, in each molecule, a polymerizable unsaturated group and any functional group selected from the group consisting of a carboxyl group, a sulfo group, and a phosphate group, and, if necessary, a compound (C) having two or more ethylenically unsaturated groups as a monomer, and polymerizing these monomers so that a ratio (weight ratio) of the acrylic acid ester (A) and the compound (B), which is (A)/(B), is 9.0/91.0 to 28.5/71.5, and, if necessary, a proportion of the compound (C) is 0.0001 to 1.5 parts by weight with respect to a total of the acrylic acid ester (A) and the compound (B) which is 100 parts by weight, and has the characteristic (1).

It should be noted that a viscosity is a value obtained by performing measurements with a B type rotational viscometer and a rotor No. 4 at a temperature of 20° C. and a rotation speed of 3 rpm.

The aqueous solution containing 1% by weight of acrylic acid ester (A)/compound (B) copolymer of the present invention and 3% by weight of ascorbyl magnesium phosphate, and having a pH of 8 preferably has a viscosity of 5,000 mPa·s or more at 20° C., more preferably 7,000 mPa·s or more, even more preferably 12,000 mPa·s or more, particularly preferably 15,000 mPa·s or more, and most preferably 20,000 mPa·s or more. In addition, an upper limit of the viscosity may vary depending on applications of the cosmetic preparation, and is, for example, 100,000 mPa·s or less. Because of such characteristics, in a case where the copolymer of the present invention is used in a cosmetic preparation, thickening can be achieved with a small additive amount, and it is possible to obtain a cosmetic preparation that has excellent feeling in use and applying properties as well as a unique tactile feeling.

In a case where the aqueous solution containing 1% by weight of acrylic acid ester (A)/compound (B) copolymer of the present invention and 3% by weight of ascorbyl magnesium phosphate, and having a pH of 8 has a viscosity of 15,000 mPa·s or more at 20° C., it is easy to maintain a high viscosity in the presence of a high concentration of an electrolyte. Thus, acrylic acid ester (A)/compound (B) copolymer of the present invention can be used in various cosmetic preparations in which a high concentration of an electrolyte is blended.

In a case where the aqueous solution containing 1% by weight of acrylic acid ester (A)/compound (B) copolymer of the present invention and 3% by weight of ascorbyl magnesium phosphate, and having a pH of 8 has a viscosity of 20,000 mPa·s or more at 20° C., it is easy to maintain a higher viscosity in the presence of very high concentration of an electrolyte. Thus, acrylic acid ester (A)/compound (B) copolymer of the present invention can be suitably used for cosmetic preparations characterized a high viscosity.

The acrylic acid ester (A)/compound (B) copolymer of the present invention is dissolved in pure water such as deionized water, and an alkali is used to make it a weakly acidic to alkaline viscous aqueous solution having a pH of 5 to 11 at a copolymer concentration of about 1% by weight, which can be used as a thickening agent for cosmetic preparation and the like. That is, the thickening agent containing acrylic acid ester (A)/compound (B) copolymer of the present invention is also contained in the present invention. The alkali for neutralization is not particularly limited, and examples thereof include alkali metal hydroxides such as sodium hydroxide and potassium hydroxide, alkaline earth metal hydroxides such as magnesium hydroxide and calcium hydroxide, and amines such as triethanolamine and diisopropanolamine. Among these, sodium hydroxide is preferable. An amount of the copolymer of the present invention blended in a cosmetic preparation is not particularly limited as long as a desired effect is exhibited. For example, in cosmetic preparation, the copolymer of the present invention is blended preferably in an amount of 0.01% to 5.0% by weight, more preferably in an amount of 0.05% to 3.0% by weight, and even more preferably in an amount of 0.1% to 1.5% by weight. From the viewpoint of thickening effects, the blending amount of the copolymer of the present invention is preferably 0.01% by weight or more, and from the viewpoint of feeling in use and applying properties, a blending amount of the copolymer of the present invention is preferably 5.0% by weight or less.

The degree of neutralization of the copolymer in a weakly acidic to alkaline viscous aqueous solution having a pH of 5 to 11 and containing acrylic acid ester (A)/compound (B) copolymer of the present invention is, for example, 30 to 100 mol %.

A viscous aqueous solution obtained by using acrylic acid ester (A)/compound (B) copolymer of the present invention is capable of achieving thickening with a small additive amount in the presence of a high concentration of an electrolyte, and has excellent feeling in use and applying properties as well as a unique tactile feeling.

The reason why acrylic acid ester (A)/compound (B) copolymer of the present invention has such characteristics is uncertain. It is presumed to be due to use of a specific amount of the (A) acrylic acid ester represented by the general formula [1]. It is presumed that a fluorine atom in the acrylic acid ester (A) in the copolymer of the present invention forms an associate with an electrolyte between polymer chains due to electrostatic interaction in an aqueous solution, thereby increasing thickening properties and decreasing effects of thinning due to the electrolyte.

It is presumed that the compound (C) according to the present invention acts as a crosslinking agent, thereby affecting the viscosity.

Therefore, acrylic acid ester (A)/compound (B) copolymer of the present invention can be used to achieve thickening with a small additive amount in the presence of a high concentration of an electrolyte, and can be used to produce a cosmetic preparation that has excellent feeling in use and applying properties as well as a unique tactile feeling.

The electrolyte used in the present invention refers to a compound which ionically dissociates in water. There are no particular limitations on a type of the electrolyte, and examples thereof include acid agents, for example, carboxylic acids such as lactic acid, gluconic acid, succinic acid, glutaric acid, adipic acid, malic acid, tartaric acid, maleic acid, fumaric acid, itaconic acid, citric acid, phthalic acid, acetic acid, benzoic acid, salicylic acid, gallic acid, diethylbarbituric acid, and hyaluronic acid; amino acids such as glycine, alanine, valine, leucine, serine, glutamic acid, and aspartic acid; organic sulfonic acids such as ethanesulfonic acid, phenolsulfonic acid, p-toluenesulfonic acid, and m-xylenesulfonic acid; aminosulfonic acids such as taurine; and inorganic acids such as hydrochloric acid; alkaline agents, for example, alkanolamines such as monoethanolamine, diethanolamine, triethanolamine, and cocamidomethylmonoethanolamine; ammonia and ammoniums such as ammonia, ammonium carbonate, monoammonium dihydrogen phosphate, and stearyl trimethyl ammonium chloride; and inorganic bases such as sodium hydroxide, potassium hydroxide, magnesium hydroxide, and calcium hydroxide; neutralization product salts of acid agents and alkaline agents such as sodium chloride, potassium chloride, magnesium chloride, calcium chloride, sodium citrate, potassium citrate, magnesium citrate, calcium citrate, sodium benzoate, potassium benzoate, magnesium benzoate, calcium benzoate, ammonium chloride, sodium carbonate, potassium carbonate, magnesium carbonate, calcium carbonate, disodium edetate, disodium phosphate, dipotassium phosphate, magnesium phosphate, calcium phosphate, monoethanolamine sulfate, sodium silicate No. 1, sodium silicate No. 2, sodium silicate No. 3, sodium cocoylmethyltaurine, sodium lauroylmethylalanine, sodium lauroylsarcosine, sodium laureth-4 carboxylate, sodium cocoylglutamate, disodium ethylenediaminetetraacetate, sodium laureth sulfate, sodium sulfite (anhydrous), trisodium ethylenediamine disuccinate, thioglycolic acid, and sodium bromate; ascorbic acid; ascorbic acid derivatives such as sodium L-ascorbyl-phosphate and magnesium L-ascorbyl-phosphate; and active ingredients such as dipotassium glycyrrhizinate. Among these electrolytes, from the viewpoints of stable blending into cosmetic preparation, and water retention, moisture retention, or the like during skin application, carboxylic acids such as lactic acid, malic acid, maleic acid, citric acid, benzoic acid, salicylic acid, and hyaluronic acid; amino acids such as glycine, alanine, valine, leucine, serine, glutamic acid, and aspartic acid; alkanolamines such as monoethanolamine, diethanolamine, triethanolamine, and cocamidomethylmonoethanolamine; inorganic bases such as sodium hydroxide, sodium hydroxide, potassium hydroxide, magnesium hydroxide, and calcium hydroxide; neutralization product salts of acid agents and alkaline agents such as sodium chloride, potassium chloride, magnesium chloride, calcium chloride, sodium citrate, potassium citrate, magnesium citrate, and calcium citrate; ascorbic acid; ascorbic acid derivatives such as sodium L-ascorbyl-phosphate and magnesium L-ascorbyl-phosphate; and dipotassium glycyrrhizinate are preferable. In addition, a blending amount of these electrolytes is usually 1 to 3,000 parts by weight with respect to 100 parts by weight of acrylic acid ester (A)/compound (B) copolymer, and preferably 5 to 2,000 parts by weight.

Among the electrolytes, depending on types of cosmetic preparation, polyvalent electrolytes such as magnesium hydroxide, calcium hydroxide, magnesium chloride, calcium chloride, magnesium citrate, calcium citrate, magnesium benzoate, calcium benzoate, magnesium carbonate, calcium carbonate, magnesium phosphate, and magnesium L-ascorbyl-phosphate may be preferable. The copolymer of the present invention is capable of forming a viscous aqueous solution having a desired viscosity in the presence of such a polyvalent electrolyte.

Examples of the cosmetic preparation of the present invention include a skin lotion, an emulsion, a beauty liquid, a cream, a cream pack, a massage cream, a cleansing cream, a cleansing gel, a facial cleansing foam, a body shampoo, a body lotion, a styling gel, a hair tonic, a hair growth agent, an anti-dandruff agent, an eyeliner, mascara, a foundation, a sunscreen, a moisturizer, an antiperspirant, a whitening agent, an anti-aging agent, and an anti-wrinkle agent.

In the cosmetic preparation of the present invention, in addition to the electrolytes, additives and the like commonly used in the field of cosmetic preparation may be contained. Examples of these additives include various components listed in the Japanese Standards of Quasi-drug Ingredients 2006 such as hair coloring agents, hair setting agents, ultraviolet ray preventing agents, whitening agents, anti-aging agents, moisturizers, softening agents, antioxidants, preservatives, anti-bacterial agents, pH adjusters, buffers, surfactants, antacids, foam enhancers, foam quality improver, oil agents, emulsifiers, dispersants, viscosity adjusters, antistatic agents, colorants, and fragrances.

The thickening agent of the present invention has a relatively low viscosity in the absence of an electrolyte. Thus, it can be said to be a very useful thickening agent in view of production efficiency of cosmetic preparation and the like. That is, in various production steps of a product, a solution before addition of a (polyvalent) electrolyte has a low viscosity, and also a step of adding an electrolyte is moved to a later step. Thus, it is possible to remarkably improve work efficiencies of a reaction step, a transfer step, a heating step, a compounding step, and the like before addition of an electrolyte.

The thickening agent of the present invention can be used for various applications besides applications for cosmetic preparation. For example, the thickening agent of the present invention can be used for applications such as a medicine (an anti-bacterial agent, an anti-fungal agent, a dental caries preventive agent, an anti-calculus agent, an anti-plaque agent, a poultice, an ointment, and the like), a soil water retention agent, an antistatic agent, and a medical waste solidifying agent.

In addition to the electrolyte, the thickening agent of the present invention may contain additives and the like commonly used in the medical field, agricultural and horticultural field, and the like. Any of these additives known in this field can be used.

EXAMPLES

Hereinafter, the present invention is specifically described based on examples and comparative examples. The present invention is not limited by these examples at all. It should be noted that % in the following examples is % by weight basis (wt/wt) unless otherwise specified.

Example 1

Synthesis of Acrylic Acid Ester (A)/Compound (B) Copolymer (1) of the Present Invention Acrylic acid (35 g, 0.49 mol; manufactured by Wako Pure Chemical Industries, Ltd.), 2-perfluorohexylethyl acrylate (10.69 g, 0.0256 mol; manufactured by Unimatec Co., Ltd.), diethylene glycol diallyl ether (0.1333 g, 0.72 mmol; manufactured by Wako Pure Chemical Industries, Ltd.), and di(4-tert-butylcyclohexyl)peroxydicarbonate (0.0734 g, 0.18 mmol; product name: Perkadox 16; manufactured by Kayaku Akzo Co., Ltd.) were added to a mixed solvent of 411 mL of cyclohexane and 45.7 mL of ethyl acetate, and the solution was uniformly mixed. The mixed solution was bubbled under a nitrogen gas atmosphere for 30 minutes to degas oxygen contained in the solution. Thereafter, the solution was heated to 55° C. over 30 minutes while stirring, and the solution was further stirred for 1 hour while maintaining the same temperature. Next, the solution was heated to 75° C. over 1 hour 30 minutes, and the solution was further stirred for 2 hours while maintaining the same temperature. After stirring, the solution was cooled to room temperature, and the copolymer (polymer) precipitated by cooling was obtained by filtration. Then, the copolymer obtained by filtration was dried under reduced pressure at 90° C. to 110° C. for 8 hours, to obtain 42.43 g of acrylic acid ester (A)/compound (B) copolymer (1) of the present invention (yield: 93%). Names of the respective components and proportions (weight ratio, weight part, molar ratio, and molar quantity) thereof in Example 1 are shown in Table 1.

Examples 2 to 20

Synthesis of Acrylic Acid Ester (A)/Compound (B) Copolymers (2) to (20) of the Present Invention copolymers (2) to (20) of the present invention In Examples 2 to 20, acrylic acid ester (A)/compound (B) copolymers (2) to (20) of the present invention were obtained in accordance with the same method as in Example 1, except that the components indicated in Table 1 were used so that proportions (weight ratio, weight part, molar ratio, and molar quantity) of the respective components were those as shown in Table 1. Names of the respective components and proportions (weight ratio, weight part, molar ratio, and molar quantity) thereof in Examples 2 to 20 are shown in Table 1.

Comparative Examples 1 to 7

Synthesis of Acrylic Acid Ester/Compound (B) Copolymers (1) to (7) for Comparison In Comparative Examples 1 to 7, the acrylic acid ester/compound (B) copolymers (1) to (7) for comparison were obtained in accordance with the same method as in Example 1, except that the components were used so that proportions (weight ratio, weight part, molar ratio, and molar quantity) of the respective components were those as shown in Table 1. Names of the respective components and proportions (weight ratio, weight part, molar ratio, and molar quantity) thereof in Comparative Examples 1 to 7 are shown in Table 1.

TABLE 1

| | Copolymer | Acrylic acid ester | Compound (B) | Compound (C) | Weight ratio of (A) to (B) (A):(B) | Parts by weight* of (C) | Molar ratio of (A) to (B) (A):(B) | Molar quantity** of (C) |
|---|---|---|---|---|---|---|---|---|
| Example 1 | Copolymer (1) of the present invention | FAAC-6 | Acrylic acid | DGBA | 23.4:76.6 | 0.29 | 5:95 | 0.14 |
| Example 2 | Copolymer (2) of the present invention | FAAC-6 | Acrylic acid | DGBA | 10.6:89.4 | 0.33 | 2:98 | 0.14 |
| Example 3 | Copolymer (3) of the present invention | FAAC-6 | Acrylic acid | DGBA | 15.2:84.8 | 0.32 | 3:97 | 0.14 |
| Example 4 | Copolymer (4) of the present invention | FAAC-6 | Acrylic acid | DGBA | 19.5:80.5 | 0.3 | 4:96 | 0.14 |
| Example 5 | Copolymer (5) of the present invention | FAAC-6 | Acrylic acid | DGBA | 27.0:73.0 | 0.28 | 6:94 | 0.14 |
| Example 6 | Copolymer (6) of the present invention | FAAC-6 | Acrylic acid | DGBA | 23.4:76.6 | 0.58 | 5:95 | 0.28 |
| Example 7 | Copolymer (7) of the present invention | FAAC-6 | Acrylic acid | DGBA | 23.4:76.6 | 1.46 | 5:95 | 0.7 |
| Example 8 | Copolymer (8) of the present invention | FAAC-6 | Acrylic acid | DGBA | 23.4:76.6 | 1.04 | 5:95 | 0.5 |
| Example 9 | Copolymer (9) of the present invention | FAAC-6 | Acrylic acid | DGBA | 23.4:76.6 | 0.83 | 5:95 | 0.4 |
| Example 10 | Copolymer (10) of the present invention | FAAC-6 | Acrylic acid | DGBA | 23.4:76.6 | 0.001 | 5:95 | 0.0005 |
| Example 11 | Copolymer (11) of the present invention | FAAC-6 | Acrylic acid | DGBA | 15.2:84.8 | 1.13 | 3:97 | 0.5 |
| Example 12 | Copolymer (12) of the present invention | FAAC-6 | Acrylic acid | Neoallyl P-30M | 23.4:76.6 | 0.4 | 5:95 | 0.14 |
| Example 13 | Copolymer (13) of the present invention | FAAC-6 | Acrylic acid | Neoallyl P-30M | 15.2:84.8 | 0.44 | 3:97 | 0.14 |
| Example 14 | Copolymer (14) of the present invention | FAAC-6 | Acrylic acid | Neoallyl P-30M | 15.2:84.8 | 0.22 | 3:97 | 0.07 |
| Example 15 | Copolymer (15) of the present invention | FAAC-6 | Acrylic acid | Neoallyl P-30M | 10.6:89.4 | 0.32 | 2:98 | 0.1 |
| Example 16 | Copolymer (16) of the present invention | FAAC-6 | Acrylic acid | MBAA | 23.4:76.6 | 0.24 | 5:95 | 0.14 |
| Example 17 | Copolymer (17) of the present invention | FAAC-6 | Acrylic acid | A-DOD-N | 15.2:84.8 | 0.48 | 3:97 | 0.14 |
| Example 18 | Copolymer (18) of the present invention | FAAC-6 | Acrylic acid | — | 23.4:76.6 | — | 5:95 | — |
| Example 19 | Copolymer (19) of the present invention | FAAC-6 | Acrylic acid | — | 19.5:80.5 | — | 4:96 | — |
| Example 20 | Copolymer (20) of the present invention | FAAC-6 | Acrylic acid | — | 27.0:73.0 | — | 6:94 | — |
| Comparative Example 1 | Copolymer (1) for comparison | FAAC-6 | Acrylic acid | DGBA | 5.5:94.5 | 0.35 | 1:99 | 0.14 |
| Comparative Example 2 | Copolymer (2) for comparison | FAAC-6 | Acrylic acid | DGBA | 30.4:69.6 | 0.27 | 7:93 | 0.14 |

TABLE 1-continued

|  | Copolymer | Acrylic acid ester | Compound (B) | Compound (C) | Weight ratio of (A) to (B) (A):(B) | Parts by weight* of (C) | Molar ratio of (A) to (B) (A):(B) | Molar quantity** of (C) |
|---|---|---|---|---|---|---|---|---|
| Comparative Example 3 | Copolymer (3) for comparison | FAAC-4 | Acrylic acid | DGBA | 24.9:75.1 | 0.29 | 7:93 | 0.14 |
| Comparative Example 4 | Copolymer (4) for comparison | FAAC-4 | Acrylic acid | DGBA | 18.9:81.1 | 0.31 | 5:95 | 0.14 |
| Comparative Example 5 | Copolymer (5) for comparison | FAAC-8 | Acrylic acid | DGBA | 27.5:72.5 | 0.28 | 5:95 | 0.14 |
| Comparative Example 6 | Copolymer (6) for comparison | DFHA | Acrylic acid | DGBA | 22.0:78.0 | 0.3 | 5:95 | 0.14 |
| Comparative Example 7 | Copolymer (7) for comparison | ATFE | Acrylic acid | DGBA | 10.1:89.9 | 0.34 | 5:95 | 0.14 |

Acrylic acid ester: Acrylic acid ester containing fluorine atom
Compound (B): Compound (B) having, in each molecue, polymerizable unsaturated group and one functional group selected from group consisting of carboxyl group, sulfo group, and phosphate group
Compound (C): Compound (C) having two or more ethylenically unsaturated groups
FAAC-6: 2-Perfluorohexylethyl acrylate
FAAC-4: 2-Perfluorobutylethyl acrylate
FAAC-8: 2-Perfluorooctylethyl acrylate
DFHA: 1H,1H,7H-dodecafluoroheptyl acrylate
ATFE: Acrylic acid-2-trifluoroethyl
DGBA: Diethylene glycol diallyl ether
Necallyl P-30M: Pentaerythritol triallyl ether
MBAA: N,N'-methylenebisacrylamide
A-DOD-N: 1,10-decanediol diacrylate
*Parts by weight of compound (C) in case where total of acrylic acid ester and compound (B) is set to be 100 parts by weight
**Molar amount of compound (C) in case where total of acrylic acid ester and compound (B) is set to be 100 moles Evaluation Examples 1 to 18

Preparation of Aqueous Solutions Containing Respective Copolymers (1) to (5), (10), (11), (14), (15), (17), and (18) of the Present Invention, Preparation of Aqueous Solutions Containing Respective Copolymers (1) to (7) for Comparison, and Measurement of Viscosity The copolymers (1) to (5), (10), (11), (14), (15), (17), and (18) of the present invention (2 g of each of the copolymers) obtained in Examples 1 to 5, 10, 11, 14, 15, 17, and 18, or the copolymers (1) to (7) for comparison (2 g of each of the copolymers) was added into 198 g of deionized water, and the copolymer was dispersed. In this manner, 1% by weight of dispersion liquid was obtained. Next, 5 N sodium hydroxide aqueous solution was added to each dispersion liquid until a pH of the dispersion liquid became 8.0±0.5 while measuring the pH thereof under stirring, and aqueous solutions containing the copolymers (1) to (5), (10), (11), (14), (15), (17), and (18) of the present invention, and aqueous solutions containing the copolymers (1) to (7) for comparison were obtained. A predetermined amount of magnesium L-ascorbyl-2-phosphate was added to each of the aqueous solutions and stirred. After magnesium L-ascorbyl-2-phosphate was completely dissolved, a viscosity of the aqueous solution was measured to check effects of an additive amount of an electrolyte (magnesium L-ascorbyl-2-phosphate; polyvalent electrolyte which is divalent) on the viscosity of the aqueous solution. It should be noted that the measured viscosity value is a value obtained by measuring viscosity with a B type rotational viscometer and a rotor No. 4 at a temperature of 20° C. and a rotation speed of 3 rpm. The results are shown in Table 2.

TABLE 2

|  |  |  | Addition amount of L-ascorbyl magnesium phosphate (wt %) | | | | |
|---|---|---|---|---|---|---|---|
|  | Copolymer | Saits | 1.00 | 1.25 | 1.50 | 1.75 | 2.00 |
| Evaluation Example 1 | Copolymer (1) of present invention | L-Ascorbyl magnesium phosphate | 49,600 | 62,200 | 45,000 | 33,000 | 30,200 |
| Evaluation Example 2 | Copolymer (2) of present invention | L-Ascorbyl magnesium phosphate | Less than 2,000 | Less than 2,000 | Less than 2,000 | Less than 2,000 | Less than 2,000 |
| Evaluation Example 3 | Copolymer (3) of present invention | L-Ascorbyl magnesium phosphate | Less than 2,000 | 7,000 | 13,800 | 17,000 | 24,200 |
| Evaluation Example 4 | Copolymer (4) of present invention | L-Ascorbyl magnesium phosphate | 23,200 | 35,600 | 35,000 | 42,800 | 32,400 |
| Evaluation Example 5 | Copolymer (5) of present invention | L-Ascorbyl magnesium phosphate | 77,200 | 58,000 | 73,600 | 50,200 | 40,200 |
| Evaluation Example 6 | Copolymer (10) of present invention | L-Ascorbyl magnesium phosphate | 21,000 | Not measured | 29,400 | Not measured | 27,000 |
| Evaluation Example 7 | Copolymer (11) of present invention | L-Ascorbyl magnesium phosphate | 50,400 | Not measured | 45,000 | Not measured | 27,200 |
| Evaluation Example 8 | Copolymer (14) of present invention | L-Ascorbyl magnesium phosphate | Less than 2,000 | Not measured | 17,600 | Not measured | 25,000 |
| Evaluation Example 9 | Copolymer (15) of present invention | L-Ascorbyl magnesium phosphate | 6,000 | Not measured | 8,000 | Not measured | 10,800 |
| Evaluation Example 10 | Copolymer (17) of present invention | L-Ascorbyl magnesium phosphate | 5,200 | Not measured | 19,000 | Not measured | 27,000 |

TABLE 2-continued

| | | | | | | | |
|---|---|---|---|---|---|---|---|
| Evaluation Example 11 | Copolymer (18) of present invention | L-Ascorbyl magnesium phosphate | 20,600 | Not measured | 29,000 | Not measured | 27,200 |
| Evaluation Example 12 | Copolymer (1) for comparison | L-Ascorbyl magnesium phosphate | Less than 2,000 | Less than 2,000 | Less than 2,000 | Less than 2,000 | Less than 2,000 |
| Evaluation Example 13 | Copolymer (2) for comparison | L-Ascorbyl magnesium phosphate | 59,400 | 65,600 | 35,000 | 22,000 | 7,200 |
| Evaluation Example 14 | Copolymer (3) for comparison | L-Ascorbyl magnesium phosphate | Less than 2,000 | Not measured | Less than 2,000 | Not measured | Less than 2,000 |
| Evaluation Example 15 | Copolymer (4) for comparison | L-Ascorbyl magnesium phosphate | Less than 2,000 | Less than 2,000 | Less than 2,000 | Less than 2,000 | Less than 2,000 |
| Evaluation Example 16 | Copolymer (5) for comparison | L-Ascorbyl magnesium phosphate | 38,000 | Not measured | Less than 2,000 | Not measured | Less than 2,000 |
| Evaluation Example 17 | Copolymer (6) for comparison | L-Ascorbyl magnesium phosphate | Less than 2,000 | Not measured | Less than 2,000 | Not measured | Less than 2,000 |
| Evaluation Example 18 | Copolymer (7) for comparison | L-Ascorbyl magnesium phosphate | Less than 2,000 | Not measured | Less than 2,000 | Not measured | Less than 2,000 |

| | Addition amount of L-ascorbyl magnesium phosphate (wt %) | | | | | | |
|---|---|---|---|---|---|---|---|
| | 2.25 | 2.50 | 3.00 | 3.50 | 4.00 | 5.00 | 6.00 |
| Evaluation Example 1 | 28,400 | 27,600 | 14,000 | 7,600 | 2,000 | Not measured | Not measured |
| Evaluation Example 2 | 2,000 | 4,000 | 5,600 | 4,800 | 4,400 | 2,200 | Less than 2,000 |
| Evaluation Example 3 | 29,600 | 31,000 | 30,400 | 37,600 | 27,600 | 26,600 | 16,000 |
| Evaluation Example 4 | 37,000 | 32,800 | 33,000 | 27,600 | 18,000 | 10,000 | 5,000 |
| Evaluation Example 5 | 32,000 | 19,200 | 8,000 | 5,800 | 2,000 | Not measured | Not measured |
| Evaluation Example 6 | Not measured | 21,000 | 11,800 | 7,000 | Not measured | Not measured | Not measured |
| Evaluation Example 7 | Not measured | 14,000 | 6,200 | Less than 2,000 | Not measured | Not measured | Not measured |
| Evaluation Example 8 | Not measured | 24,000 | 21,000 | 12,000 | 8,800 | 3,000 | Not measured |
| Evaluation Example 9 | Not measured | 12,200 | 10,800 | 10,000 | 7,000 | Not measured | Not measured |
| Evaluation Example 10 | Not measured | 22,800 | 15,000 | 10,400 | 3,000 | Less than 2,000 | Not measured |
| Evaluation Example 11 | Not measured | 20,600 | 12,000 | 6,600 | 2,800 | Not measured | Not measured |
| Evaluation Example 12 | Less than 2,000 | Less than 2,000 | Less than 2,000 | Less than 2,000 | Less than 2,000 | Less than 2,000 | Not measured |
| Evaluation Example 13 | 3,800 | Less than 2,000 | Not measured | Not measured | Not measured | Not measured | Not measured |
| Evaluation Example 14 | Not measured | Less than 2,000 | Less than 2,000 | Less than 2,000 | Not measured | Not measured | Not measured |
| Evaluation Example 15 | Less than 2,000 | Less than 2,000 | Less than 2,000 | Less than 2,000 | Less than 2,000 | Not measured | Not measured |
| Evaluation Example 16 | Not measured | Less than 2,000 | Less than 2,000 | Less than 2,000 | Less than 2,000 | Not measured | Not measured |
| Evaluation Example 17 | Not measured | Less than 2,000 | Less than 2,000 | Less than 2,000 | Less than 2,000 | Not measured | Not measured |
| Evaluation Example 18 | Not measured | Less than 2,000 | Less than 2,000 | Less than 2,000 | Less than 2,000 | Not measured | Not measured |

As is clearly shown from the results of Evaluation Examples 1 to 18, it was found that the aqueous solution containing the copolymer of the present invention has a viscosity of 5,000 mPa·s or more even in a case where a polyvalent electrolyte such as magnesium L-ascorbyl-2-phosphate at a high concentration (3% by weight) is contained therein. Therefore, it was found that the copolymer of the present invention is capable of forming a viscous aqueous solution having a desired viscosity in the presence of an electrolyte, in particular, a polyvalent electrolyte, and is capable of maintaining the desired viscosity even in a case where the electrolyte is present at a high concentration. As described above, the copolymer of the present invention contains, as components of the copolymer, predetermined amounts of a fluorine-containing acrylic acid ester having a specific structure and, if necessary, a crosslinking agent component. Thus, it was found that the copolymer has thickening effects and salt-resistant effects in the presence of an electrolyte. As described above, acrylic acid ester (A)/compound (B) copolymer of the present invention is capable of forming a viscous aqueous solution having a desired viscosity in the presence of an electrolyte, in particular, a polyvalent electrolyte. Thus, the copolymer can be used as a thickening agent having good thickening and salt-resistant properties, and can be expected as a thickening agent which is, for example, used for cosmetic preparation and the like.

In addition, the aqueous solution containing the copolymer of the present invention in which a ratio (weight ratio) of acrylic acid ester (A) and compound (B), which is (A)/(B), falls within a range of 14.0/86.0 to 25.0/75.0 has a viscosity of 12,000 mPa·s or more in a case where 3% by weight of magnesium L-ascorbyl-2-phosphate is added. Thus, it was found that the aqueous solution can be suitably used for various cosmetic preparations in which a high concentration of an electrolyte coexists.

Furthermore, the aqueous solution containing the copolymer of the present invention in which a ratio (weight ratio) of acrylic acid ester (A) and compound (B), which is (A)/(B), falls within a range of 14.5/85.5 to 20.0/80.0 has a viscosity of 15,000 mPa·s or more in a case where 3% by weight of magnesium L-ascorbyl-2-phosphate is added. Thus, it was found that the aqueous solution can be suitably used for cosmetic preparation characterized by a high viscosity.

Evaluation Examples 19 to 22

Sensitivity Test of Aqueous Solutions Containing Copolymers (1), (3), and (18) of the Present Invention, and Sensitivity Test of Aqueous Solution Containing General Carbomer Each of the copolymers (1), (3), and (18) of the present invention obtained in Examples 1, 3, and 18, or "copolymer including acrylic acid, acrylic acid long-chain alkyl ester, and crosslinking agent" (copolymer (8) for comparison) (trade name: AQUPEC, manufactured by Sumitomo Seika Chemicals Co., Ltd.) was added in deionized water, the copolymer was dispersed. In this manner, 1% by weight of dispersion liquid was obtained. Next, 5 N sodium hydroxide aqueous solution was added to each dispersion liquid until a pH of the dispersion liquid became 7.0±0.5 while measuring the pH thereof under stirring. Then, sodium chloride was added thereto so that the dispersion liquid had a viscosity of about 5,000 mPa·s. Aqueous solutions containing the copolymers (1), (3), and (18) of the present invention, and an aqueous solution containing the copolymer (8) for comparison were obtained.

For each of the aqueous solutions, 5 male and 5 female individuals were set as subjects, and evaluations were performed on the following items. The results are shown in Table 3.

1) Feeling in Use

The feeling in use in a case where the copolymer was used for cosmetic application was evaluated in two items of a degree of liquid cutting (ease of application) and tactile feeling.

The degree of liquid cutting (ease of application) was evaluated based on whether liquid cutting was good or poor in a case where each aqueous solution was scooped. Evaluations were performed in the following four levels from a total point of 10 individuals in which 2 points are given in a case of good liquid cutting, 1 point is given in a case of a slightly good liquid cutting, and 0 points are given in a case of slightly poor liquid cutting.

The tactile feeling was evaluated by tactile feeling in a case where each aqueous solution was touched with a finger. Evaluations were performed in the following four levels from a total of 10 individuals in which 2 points are given in case where there is a jiggly tactile feeling (elastic tactile feeling), 1 point is given in a case where there is a slightly jiggly tactile feeling (slightly elastic tactile feeling), and 0 points are given in a case where there is no jiggly tactile feeling (elastic tactile feeling).

Total point of 18 points or more: A
Total point of equal to or greater than 15 points and fewer than 18 points: B
Total point of equal to or greater than 10 points and fewer than 15 points: C
Total point of fewer than 10 points: D 2) Applying Properties Applying properties were evaluated by placing a drop of each aqueous solution on a back of the hand of the subject with a dropper and determining whether it is difficult to drip in a case where the back was made vertical. Evaluations were performed in the following four levels from a total point of 10 individuals in which 2 points are given in a case where it is difficult to drip, 1 point is given in a case where it is slightly difficult to drip, and 0 points are given in a case where it is easy to drip.

Total point of 18 points or more: A
Total point of equal to or greater than 15 points and fewer than 18 points: B
Total point of equal to or greater than 10 points and fewer than 15 points: C
Total point of fewer than 10 points: D 3) Transparency Regarding transparency, each solution was visually observed and evaluated on whether it has transparency. Evaluations were performed in the following four levels from a total point of 10 individuals in which 2 points are given in a case where there is transparency, 1 point is given in a case where there is slight transparency, and 0 points are given in a case where there is poor transparency.

Total point of 18 points or more: A
Total point of equal to or greater than 15 points and fewer than 18 points: B
Total point of equal to or greater than 10 points and fewer than 15 points: C
Total point of fewer than 10 points: D Table 3

|  | Copolymer | 1) Feeling in use | | 2) Applying properties | 3) Transparency |
| --- | --- | --- | --- | --- | --- |
|  |  | Liquid draining | Feeling of softness |  |  |
| Evaluation Example 19 | Copolymer (1) of the present invention | B (17 points) | A (20 pointss) | B (16 points) | A (20 pointss) |
| Evaluation Example 20 | Copolymer (3) of the present invention | B (18 points) | A (19 points) | A (19 points) | A (19 points) |
| Evaluation Example 21 | Copolymer (18) of the present invention | B (16 points) | B (17 points) | B (16 points) | B (15 points) |
| Evaluation Example 22 | Copolymer (8) for comparison | C (12 points) | D (0 points) | C (14 points) | D (6 points) |

As is clearly shown from the results of Evaluation Examples 19 to 22, it was found that the aqueous solution containing the copolymer (8) for comparison had insufficient liquid cutting and applying properties, and also had no elastic tactile feeling. On the other hand, the aqueous solution containing the copolymer of the present invention has an excellent degree of liquid cutting, has a jiggly tactile feeling (elastic tactile feeling), hardly drips, has good applying properties. Thus, the aqueous solution can be expected as a thickening agent which is used for cosmetic preparation having excellent feeling in use and a unique tactile feeling.

In addition, the aqueous solution containing the copolymer (1) or (3) of the present invention is excellent in appearance transparency. Thus, the aqueous solution can be, for example, suitably used for cosmetics characterized by colorlessness such as a skin lotion or a beauty liquid.

It is presumed that the characteristics of the aqueous solution containing the copolymer of the present invention are caused by having the constitutional unit derived from the acrylic acid ester represented by the general formula [1] in the copolymer.

Example 21

Preparation of Skin Lotion Using the Acrylic Acid Ester (A)/Compound (B) Copolymer (3) of the Present Invention Component 1 was added to a part of Component 11 so that swelling occurred, and then Component 2 was added while stirring to adjust the pH to 8.0. Next, Components 3 to 9 were added, and uniformly stirred and mixed. Finally, Components 10 and 11 were added to prepare a skin lotion. Names of the respective components and proportions (% by weight) thereof in Example 21 are shown in Table 4.

TABLE 4

| Component No. | Component | Blending amount (%) |
| --- | --- | --- |
| 1 | Copolymer (3) of present invention | 1.00 |
| 2 | 5N Sodium hydroxide | To adjust pH to 8.0 |
| 3 | Magnesium L-ascorbyl-2-phosphate | 3.00 |
| 4 | Citric acid | 0.01 |
| 5 | Sodium monohydrogenphosphate | 0.10 |
| 6 | Ethanol | 8.00 |
| 7 | Polyoxyethylene hardened castor oil | 0.30 |
| 8 | Phenoxyethanol | 0.10 |
| 9 | Hyaluronic acid | 0.05 |
| 10 | Fragrance | 0.20 |
| 11 | Purified water | Proportion to make total of 100.0 |

The skin lotion obtained in Example 21 had a shape without dripping. In addition, acrylic acid ester (A)/compound (B) copolymer of the present invention did not aggregate.

Example 22

Preparation of Emulsion Using Acrylic Acid Ester (A)/Compound (B) Copolymer (3) of the Present Invention Components 1 to 7; and Components 8, 13, 14, and a part of Component 16 were stirred and mixed at respective proportions, and heated to 80° C. The latter was added dropwise to the former, and then emulsification was performed by stirring. Next, a viscosity was adjusted with Component 9 by setting the pH to 8.0, and Components 10 to 12 were further added and cooled. Finally, Components 15 and 16 were added to prepare an emulsion. Names of the respective components and proportions (% by weight) thereof in Example 22 are shown in Table 5.

TABLE 5

| Component No. | Component | Blending amount (%) |
| --- | --- | --- |
| 1 | Polyoxyethylene sorbitan monostearate | 1.00 |
| 2 | Polyoxypropylene sorbitol tetraoleate | 1.50 |
| 3 | Lipophilic glyceryl monostearate | 0.50 |
| 4 | Stearic acid | 0.50 |
| 5 | Behenyl alcohol | 1.50 |
| 6 | Squalane | 5.00 |
| 7 | Cetyl 2-ethylhexanoate | 5.00 |
| 8 | Copolymer (3) of present invention | 1.00 |
| 9 | 5N Sodium hydroxide | To adjust pH to 8.0 |
| 10 | Sodium lactate | 1.00 |
| 11 | Citric acid | 0.01 |
| 12 | Sodium monohydrogenphosphate | 0.10 |
| 13 | 1,3-Butylene glycol | 7.00 |
| 14 | Pentane diol | 0.10 |
| 15 | Fragrance | 0.20 |
| 16 | Purified water | Proportion to make total of 100.0 |

The emulsion obtained in Example 22 had a shape without dripping. In addition, acrylic acid ester (A)/compound (B) copolymer of the present invention did not aggregate.

Example 23

Preparation of Beauty Liquid Using Acrylic Acid Ester (A)/Compound (B) Copolymer (3) of the Present Invention Component 1 was added to a part of Component 12 so that swelling occurred, and then Component 2 was added while stirring to adjust the pH to 8.0. Next, Components 3 to 10, and a part of Component 12 were mixed and dissolved at respective proportions at an ordinary temperature, and the mixture was allowed to a viscous water-soluble liquid while stirring. Finally, Components 11 and 12 were added to prepare a beauty liquid. Names of the respective components and proportions (% by weight) thereof in Example 23 are shown in Table 6.

TABLE 6

| Component No. | Component | Blending amount (%) |
| --- | --- | --- |
| 1 | Copolymer (3) of present invention | 1.00 |
| 2 | 5N Sodium hydroxide | To adjust pH to 8.0 |
| 3 | Ascorbic acid 2-glucoside | 3.00 |
| 4 | Sodium citrate | 0.50 |
| 5 | Tetrasodium edetate | 0.10 |
| 6 | 1,3-Butylene glycol | 7.00 |
| 7 | Glycerin | 8.00 |
| 8 | Sodium hyaluronate | 0.20 |
| 9 | Phenoxyethanol | 0.15 |
| 10 | Ethanol | 5.00 |
| 11 | Fragrance | 0.20 |
| 12 | Purified water | Proportion to make total of 100.0 |

The beauty liquid obtained in Example 23 had a shape without dripping. In addition, acrylic acid ester (A)/compound (B) copolymer of the present invention did not aggregate.

Example 24

Preparation of Cream Using Acrylic Acid Ester (A)/Compound (B) Copolymer (3) of the Present Invention Components 1 to 6; and Components 7, 9 to 11, 13, and a part of Component 15 were stirred and mixed at respective proportions, and heated to 80° C. The latter was added dropwise to the former, and then emulsification was performed by stirring. Next, a viscosity was adjusted with Component 12 and a part of Component 15 by setting the pH to 8.0, and Component 8 and a part of Component 15 were further added and cooled. Finally, Components 14 and 15 were added to prepare a cream. Names of the respective components and proportions (% by weight) thereof in Example 24 are shown in Table 7.

TABLE 7

| Component No. | Component | Blending amount (%) |
|---|---|---|
| 1 | Decaglyceryl pentaoleate | 3.00 |
| 2 | Beeswax | 2.00 |
| 3 | Cetanol | 2.00 |
| 4 | Squalane | 5.00 |
| 5 | Glyceryl tri-2-ethylhexanoate | 2.00 |
| 6 | Dimethyl polysiloxane | 0.50 |
| 7 | Glycerin | 5.00 |
| 8 | Magnesium L-ascorbyl-2-phosphate | 3.00 |
| 9 | Sodium citrate | 0.50 |
| 10 | Tetrasodium edetate | 0.10 |
| 11 | Copolymer (3) of present invention | 1.00 |
| 12 | 5N Sodium hydroxide | To adjust pH to 8.0 |
| 13 | Phenoxyethanol | 0.10 |
| 14 | Fragrance | 0.20 |
| 15 | Purified water | Proportion to make total of 100.0 |

The cream obtained in Example 24 had a shape without dripping. In addition, acrylic acid ester (A)/compound (B) copolymer of the present invention did not aggregate.

Example 25

Preparation of Cream Pack Using Acrylic Acid Ester (A)/Compound (B) Copolymer (3) of the Present Invention Components 1 to 3; and Components 4 to 6, 9, and a part of Component 11 were stirred and mixed at respective proportions, and heated to 80° C. The latter was added dropwise to the former, and then emulsification was performed by stirring. Next, a viscosity was adjusted with Component 7 and a part of Component 11 by setting the pH to 8.0, and Component 8 and a part of Component 11 were further added and cooled. Finally, Components 10 and 11 were added to prepare a cream pack. Names of the respective components and proportions (% by weight) thereof in Example 25 are shown in Table 8.

TABLE 8

| Component No. | Component | Blending amount (%) |
|---|---|---|
| 1 | Polyoxyethylene polyoxypropylene cetyl ether | 0.70 |
| 2 | Diglyceryl monostearate | 0.30 |
| 3 | Jojoba oil | 1.00 |
| 4 | Glycerin | 5.00 |
| 5 | 1,3-Butylene glycol | 3.00 |
| 6 | Copolymer (3) of present invention | 1.00 |
| 7 | 5N Sodium hydroxide | To adjust pH to 8.0 |
| 8 | Magnesium L-ascorbyl-2-phosphate | 2.00 |
| 9 | Phenoxyethanol | 0.15 |
| 10 | Fragrance | 0.20 |
| 11 | Purified water | Proportion to make total of 100.0 |

The cream pack obtained in Example 25 had a shape without dripping. In addition, acrylic acid ester (A)/compound (B) copolymer of the present invention did not aggregate.

Example 26

Preparation of Massage Cream Using Acrylic Acid Ester (A)/Compound (B) Copolymer (3) of the Present Invention Components 1 to 7; and Components 8, 10, 12, and a part of Component 14 were stirred and mixed at respective proportions, and heated to 80° C. The latter was added dropwise to the former, and then emulsification was performed by stirring. Next, a viscosity was adjusted with Component 9 and a part of Component 14 by setting the pH to 8.0, and Component 11 and a part of Component 14 were further added and cooled. Finally, Components 13 and 14 were added to prepare a massage cream. Names of the respective components and proportions (% by weight) thereof in Example 26 are shown in Table 9.

TABLE 9

| Component No. | Component | Blending amount (%) |
|---|---|---|
| 1 | Polyoxyethylene cetyl ether | 2.00 |
| 2 | Lipophilic glyceryl monostearate | 4.00 |
| 3 | Cetanol | 2.00 |
| 4 | White vaseline | 6.00 |
| 5 | Squalane | 30.00 |
| 6 | Glyceryl tri-2-ethylhexanoate | 5.00 |
| 7 | Dimethyl polysiloxane | 0.50 |
| 8 | Copolymer (3) of present invention | 1.00 |
| 9 | 5N Sodium hydroxide | To adjust pH to 8.0 |
| 10 | Glycerin | 5.00 |
| 11 | Sodium pyrrolidone carboxylate | 1.00 |
| 12 | Methylparaben | 0.15 |
| 13 | Fragrance | 0.20 |
| 14 | Purified water | Proportion to make total of 100.0 |

The massage cream obtained in Example 26 had a shape without dripping. In addition, acrylic acid ester (A)/compound (B) copolymer of the present invention did not aggregate.

Example 27

Preparation of Cleansing Gel Using Acrylic Acid Ester (A)/Compound (B) Copolymer (3) of the Present Invention Components 4 and 5; and Components 1, 6, 7, and a part of Component 9 were stirred and mixed at respective proportions, and heated to 80° C. The latter was added dropwise to the former, and then emulsification was performed by stirring. Next, a viscosity was adjusted with Component 2 and a part of Component 9 by setting the pH to 8.0, and Component 3 and a part of Component 9 were further added and cooled. Finally, Components 8 and 9 were added to prepare a cleansing gel. Names of the respective components and proportions (% by weight) thereof in Example 27 are shown in Table 10.

TABLE 10

| Component No. | Component | Blending amount (%) |
|---|---|---|
| 1 | Copolymer (3) of present invention | 1.00 |
| 2 | 5N Sodium hydroxide | To adjust pH to 8.0 |
| 3 | Sodium pyrrolidone carboxylate | 1.00 |
| 4 | Polyoxyethylene cetyl ether | 15.00 |
| 5 | Polyoxyethylene lauryl ether | 10.00 |
| 6 | 1,3-Butylene glycol | 8.00 |
| 7 | Phenoxyethanol | 0.15 |
| 8 | Fragrance | 0.20 |
| 9 | Purified water | Proportion to make total of 100.0 |

The cleansing gel obtained in Example 27 had a shape without dripping. In addition, acrylic acid ester (A)/compound (B) copolymer of the present invention did not aggregate.

Example 28

Preparation of Facial Cleansing foam Using Acrylic Acid Ester (A)/Compound (B) Copolymer (3) of the Present Invention Components 1 to 6 were stirred and mixed at respective proportions, and heated to 80° C. Next, Components 7 to 9, 12, 13, and a part of Component 15 was stirred and mixed at respective proportions, and the mixture was heated to 80° C. and added thereto. The resulting product was mixed. Next, Component 10 and a part of Component 15 were added to adjust a viscosity. Further, Component 11 and a part of Component 15 were added while stirring to adjust the pH to 8.5, and cooled. Finally, Components 14 and 15 were added to prepare a facial cleansing foam. Names of the respective components and proportions (% by weight) thereof in Example 28 are shown in Table 11.

TABLE 11

| Component No. | Component | Blending amount (%) |
|---|---|---|
| 1 | Myristic acid | 15.00 |
| 2 | Palmitic acid | 5.00 |
| 3 | Stearic acid | 3.00 |
| 4 | Beeswax | 3.00 |
| 5 | Ethylene glycol distearate | 2.00 |
| 6 | Coconut oil fatty acid diethanol amide | 3.00 |
| 7 | Glycerin | 10.00 |
| 8 | Hydrolyzed collagen | 0.02 |
| 9 | Copolymer (3) of present invention | 1.00 |
| 10 | 5N Sodium hydroxide | Adequate amount |
| 11 | 5N Potassium hydroxide | Adequate amount to adjust pH to 8.5 |
| 12 | Sodium lauroyl methyl alanine | 10.00 |
| 13 | Methylparaben | 0.15 |
| 14 | Fragrance | 0.20 |
| 15 | Purified water | Proportion to make total of 100.0 |

The facial cleansing foam obtained in Example 28 had a shape without dripping. In addition, acrylic acid ester (A)/compound (B) copolymer of the present invention did not aggregate.

Example 29

Preparation of Sunscreen Using Acrylic Acid Ester (A)/Compound (B) Copolymer (3) of the Present Invention A part of Component 1 and Components 4 to 8; and a remainder of Component 1 and Components 9 to 13 were stirred and mixed at respective proportions, and heated to 80° C. The latter was added dropwise to the former, and then emulsification was performed by stirring. Next, a viscosity was adjusted with Component 2 and a part of Component 16 by setting the pH to 8.0, and Component 3 and a part of Component 16 were further added and cooled. Finally, Components 14, 15, and a part of Component 16 were added to prepare a sunscreen. Names of the respective components and proportions (% by weight) thereof in Example 29 are shown in Table 12.

TABLE 12

| Component No. | Component | Blending amount (%) |
|---|---|---|
| 1 | Copolymer (3) of present invention | 1.00 |
| 2 | 5N Sodium hydroxide | To adjust pH to 8.0 |
| 3 | Ascorbic acid 2-glucoside | 2.00 |
| 4 | Citric acid | 0.01 |
| 5 | Sodium monohydrogenphosphate | 0.10 |
| 6 | Preservative | 0.15 |
| 7 | 1,3-Butylene glycol | 7.00 |
| 8 | Glycerin | 8.00 |
| 9 | Sorbitan monostearate | 0.50 |
| 10 | Polyoxyethylene sorbitan monooleate | 0.50 |
| 11 | Sorbitan sesquioleate | 0.50 |
| 12 | Cetanol | 2.00 |
| 13 | 2-Ethylhexyl paramethoxycinnamate | 10.00 |
| 14 | Ethanol | 10.00 |
| 15 | Fragrance | 0.20 |
| 16 | Purified water | Proportion to make total of 100.0 |

The sunscreen obtained in Example 29 had a shape without dripping. In addition, acrylic acid ester (A)/compound (B) copolymer of the present invention did not aggregate.

Example 30

Preparation of Styling Gel Using Acrylic Acid Ester (A)/Compound (B) Copolymer (3) of the Present Invention Components 1, 2, 4, 6, and a part of Component 8 were dissolved at respective proportions at an ordinary temperature, then the pH thereof was brought to 8.0 with Component 3 and a part of Component 8, and Component 5 and a part of Component 8 were further added and mixed. Finally, Components 7 and 8 were added to prepare a styling gel. Names of the respective components and proportions (% by weight) thereof in Example 30 are shown in Table 13.

TABLE 13

| Component No. | Component | Blending amount (%) |
|---|---|---|
| 1 | Carboxyvinyl polymer | 0.10 |
| 2 | Copolymer (3) of present invention | 1.00 |
| 3 | 5N Sodium hydroxide | To adjust pH to 8.0 |
| 4 | Vinyl pyrrolidone-vinyl acetate copolymer solution | 10.00 |
| 5 | Sodium pyrrolidone carboxylate | 1.00 |
| 6 | Methylparaben | 0.10 |
| 7 | Fragrance | 0.20 |
| 8 | Purified water | Proportion to make total of 100.0 |

The styling gel obtained in Example 30 had a shape without dripping. In addition, acrylic acid ester (A)/compound (B) copolymer of the present invention did not aggregate.

Example 31

Preparation of Eyeliner Using Acrylic Acid Ester (A)/Compound (B) Copolymer (3) of the Present Invention Components 1, 2, 4, 6, 8, and a part of Component 10 were dissolved at respective proportions at an ordinary temperature, then the pH thereof was brought to 8.0 with Component 5, and Components 3, 7, and a part of Component 10 were further added and mixed. Finally, Components 9 and 10 were added to prepare eyeliner. Names of the respective components and proportions (% by weight) thereof in Example 31 are shown in Table 14.

TABLE 14

| Component No. | Component | Blending amount (%) |
|---|---|---|
| 1 | Alkyl acrylate copolymer emulsion | 30.00 |
| 2 | 1,3-Butylene glycol | 15.00 |
| 3 | Black iron oxide | 15.00 |
| 4 | Copolymer (3) of present invention | 1.00 |
| 5 | 5N Sodium hydroxide | To adjust pH to 8.0 |
| 6 | Sodium carboxymethyl cellulose | 2.00 |
| 7 | Sodium chloride | 0.50 |
| 8 | Methylparaben | 0.15 |
| 9 | Fragrance | 0.20 |
| 10 | Purified water | Proportion to make total of 100.0 |

The eyeliner obtained in Example 31 had a shape without dripping. In addition, acrylic acid ester (A)/compound (B) copolymer of the present invention did not aggregate.

Example 32

Preparation of Mascara Using Acrylic Acid Ester (A)/Compound (B) Copolymer (3) of the Present Invention Components 1 to 5; and Components 6, 8, 11 to 14, and a part of Component 16 were stirred and mixed at respective proportions, and heated to 80° C. The latter was added dropwise to the former, and then emulsification was performed by stirring. Next, a viscosity was adjusted with Component 7 and a part of Component 16 by setting the pH to 8.0, and Components 9 and 10 were further added and cooled. Finally, Components 15 and 16 were added to prepare mascara. Names of the respective components and proportions (% by weight) thereof in Example 32 are shown in Table 15.

TABLE 15

| Component No. | Component | Blending amount (%) |
|---|---|---|
| 1 | Stearic acid | 2.00 |
| 2 | Carnauba wax | 2.00 |
| 3 | Beeswax | 3.00 |
| 4 | Polyoxyethylene sorbitan monooleate (20 E.O.) | 1.00 |
| 5 | Sorbitan sesquioleate | 0.50 |
| 6 | Alkyl acrylate copolymer emulsion (YODOSOLGH 810 manufactured by NSC Japan) | 1.00 |
| 7 | Triethanolamine | To adjust pH to 8.0 |
| 8 | Propyleneglycol | 1.00 |
| 9 | Black iron oxide | 10.00 |

TABLE 15-continued

| Component No. | Component | Blending amount (%) |
|---|---|---|
| 10 | Kaolin | 10.00 |
| 11 | Copolymer (3) of present invention | 1.00 |
| 12 | Sodium carboxymethyl cellulose | 2.00 |
| 13 | Sodium chloride | 0.20 |
| 14 | Preservative | 0.15 |
| 15 | Fragrance | 0.20 |
| 16 | Purified water | Proportion to make total of 100.0 |

The mascara obtained in Example 32 had a shape without dripping. In addition, acrylic acid ester (A)/compound (B) copolymer of the present invention did not aggregate.

Example 33

Preparation of Foundation Using Acrylic Acid Ester (A)/Compound (B) Copolymer (3) of the Present Invention Components 1 to 5 and 11; and Components 12, 13, 15, and a part of Component 17 were stirred and mixed at respective proportions, and heated to 80° C. The latter was added to the former, and mixing was performed. Next, the pH thereof was brought to 8.0 with Component 14 and a part of Component 17, and Components 6 to 10, and a part of Component 17 were further added and cooled while stirring. Finally, Components 16 and 17 were added to prepare a foundation. Names of the respective components and proportions (% by weight) thereof in Example 33 are shown in Table 16.

TABLE 16

| Component No. | Component | Blending amount (%) |
|---|---|---|
| 1 | Lipophilic glyceryl monostearate | 1.00 |
| 2 | Stearic acid | 5.00 |
| 3 | Behenyl alcohol | 1.00 |
| 4 | Cetanol | 0.50 |
| 5 | Squalane | 5.00 |
| 6 | Titanium oxide | 4.00 |
| 7 | Bengara | 0.50 |
| 8 | Yellow iron oxide | 1.00 |
| 9 | Black iron oxide | 0.03 |
| 10 | Talc | 4.00 |
| 11 | Soybean phospholipid | 0.30 |
| 12 | 1,3-Butylene glycol | 8.00 |
| 13 | Copolymer (3) of present invention | 1.00 |
| 14 | Triethanolamine | To adjust pH to 8.0 |
| 15 | Phenoxyethanol | 0.10 |
| 16 | Fragrance | 0.20 |
| 17 | Purified water | Proportion to make total of 100.0 |

The foundation obtained in Example 33 had a shape without dripping. In addition, acrylic acid ester (A)/compound (B) copolymer of the present invention did not aggregate.

Example 34

Preparation of Cleansing Gel Using Acrylic Acid Ester (A)/Compound (B) Copolymer (3) of the Present Invention Components 1, 5 to 8, and a part of Component 10 were mixed at respective proportions and stirred until they became uniform. Next, Component 2 was added so that the pH reached 8.0, and the mixture was stirred until a uniform gel state was obtained. Components 3, 4, and a part of Component 10 were further added and mixed. Finally, Components 9 and 10 were added to prepare a cleansing gel.

Names of the respective components and proportions (% by weight) thereof in Example 34 are shown in Table 17.

TABLE 17

| Component No. | Component | Blending amount (%) |
| --- | --- | --- |
| 1 | Copolymer (3) of present invention | 1.00 |
| 2 | 5N Potassium hydroxide | To adjust pH to 8.0 |
| 3 | Sodium chloride | 0.50 |
| 4 | Lactic acid | 0.01 |
| 5 | Phenoxyethanol | 0.15 |
| 6 | Ethanol | 10.00 |
| 7 | 1,3-Butylene glycol | 5.00 |
| 8 | Sodium cocoyl methyl taurine | 5.00 |
| 9 | Fragrance | 0.20 |
| 10 | Purified water | Proportion to make total of 100.0 |

The cleansing gel obtained in Example 34 had a shape without dripping. In addition, acrylic acid ester (A)/compound (B) copolymer of the present invention did not aggregate.

Example 35

Preparation of Facial Cleansing Foam Using Acrylic Acid Ester (A)/Compound (B) Copolymer (3) of the Present Invention Components 1 to 6 were mixed at respective proportions, heated to 80° C., and Components 7, 8, 10, and a part of Component 13, which had been uniformly mixed beforehand, were added and stirred. Next, a viscosity was adjusted with Component 9 and a part of Component 13 by setting the pH to 8.0, and Component 11 and a part of Component 13 were further added and cooled to 30° C. while stirring. Finally, Components 12 and 13 were added to prepare a facial cleansing foam. Names of the respective components and proportions (% by weight) thereof in Example 35 are shown in Table 18.

TABLE 18

| Component No. | Component | Blending amount (%) |
| --- | --- | --- |
| 1 | Myristic acid | 15.00 |
| 2 | Palmitic acid | 5.00 |
| 3 | Stearic acid | 3.00 |
| 4 | Glyceryl stearate | 3.00 |
| 5 | Ethylene glycol distearate | 2.00 |
| 6 | Coconut oil fatty acid diethanolamide | 3.00 |
| 7 | Glycerin | 15.00 |
| 8 | Preservative | 0.15 |
| 9 | 5N Potassium hydroxide | To adjust pH to 8.0 |
| 10 | Copolymer (3) of present invention | 1.00 |
| 11 | Potassium chloride | 0.05 |
| 12 | Fragrance | 0.20 |
| 13 | Purified water | Proportion to make total of 100.0 |

The facial cleansing foam obtained in Example 35 had a shape without dripping. In addition, acrylic acid ester (A)/compound (B) copolymer of the present invention did not aggregate.

Example 36

Preparation of Facial Cleansing Foam Using Acrylic Acid Ester (A)/Compound (B) Copolymer (3) of the Present Invention Components 1 to 2 were mixed at respective proportions, heated to 80° C., and Components 4, 7 to 10, and a part of Component 12, which had been uniformly mixed beforehand, were added and stirred. Next, Component 5 and a part of Component 12 were added to adjust a viscosity. Then, Components 3, 6, and a part of Component 12 were further added and cooled to 30° C. while stirring. Finally, Components 11 and 12 were added to prepare a facial cleansing foam. Names of the respective components and proportions (% by weight) thereof in Example 36 are shown in Table 19.

TABLE 19

| Component No. | Component | Blending amount (%) |
| --- | --- | --- |
| 1 | Sodium N-lauroyl glutamate | 10.00 |
| 2 | Polyoxyethylene lauryl ether (20 E.O.) | 2.00 |
| 3 | Ascorbic acid glucoside | 2.00 |
| 4 | Copolymer (3) of present invention | 1.00 |
| 5 | 5N Sodium hydroxide | 0.30 |
| 6 | Sodium chloride | 0.50 |
| 7 | Sodium citrate | Adequate amount |
| 8 | Citric acid | Adequate amount to adjust pH to 8.0 |
| 9 | Silk protein | 0.50 |
| 10 | Preservative | 0.10 |
| 11 | Fragrance | 0.20 |
| 12 | Purified water | Proportion to make total of 100.0 |

The facial cleansing foam obtained in Example 36 had a shape without dripping. In addition, acrylic acid ester (A)/compound (B) copolymer of the present invention did not aggregate.

Example 37

Preparation of Body Shampoo Using Acrylic Acid Ester (A)/Compound (B) Copolymer (3) of the Present Invention Components 1 to 3 were mixed at respective proportions, heated to 80° C., and Components 5 to 7, 10, 11, and a part of Component 13, which had been uniformly mixed beforehand, were slowly added and stirred until they became uniform. Next, the viscosity was adjusted with Component 8 and a part of Component 13 by setting the pH to 8.5, and Components 4, 9, and a part of Component 13 were further added and cooled to 30° C. while stirring. Finally, Components 12 and 13 were added to prepare a body shampoo. Names of the respective components and proportions (% by weight) thereof in Example 37 are shown in Table 20.

TABLE 20

| Component No. | Component | Blending amount (%) |
| --- | --- | --- |
| 1 | Triethanolamine myristate | 10.0 |
| 2 | Potassium laurate | 15.0 |
| 3 | Aminoethylaminopropylsiloxane-dimethylsiloxane copolymer | 2.0 |
| 4 | Bentonite | 1.0 |
| 5 | Glycerin | 5.0 |
| 6 | Propylene glycol | 5.0 |
| 7 | Copolymer (3) of present invention | 1.0 |
| 8 | 5N Sodium hydroxide | To adjust pH to 85 |
| 9 | Sodium chloride | 0.4 |
| 10 | Glycine | 0.5 |
| 11 | Methylparaben | 0.2 |
| 12 | Fragrance | 0.2 |
| 13 | Purified water | Proportion to make total of 100.0 |

The body shampoo obtained in Example 37 had a shape without dripping. In addition, acrylic acid ester (A)/compound (B) copolymer of the present invention did not aggregate.

Example 38

Preparation of Deodorant Gel Using Acrylic Acid Ester (A)/Compound (B) Copolymer (3) of the Present Invention Components 5 and 6 were mixed with a part of Component 15 so that swelling occurred. Then, Components 7 and a part of Component 15 were added to neutralize the mixture. Next, Components 8 to 13, and a part of Component 15 were added and mixed. Then, Components 1 to 4 were further added and uniformly mixed. Finally, Components 14 and 15 were added to prepare a deodorant gel. Names of the respective components and proportions (% by weight) thereof in Example 38 are shown in Table 21.

TABLE 21

| Component No. | Component | Blending amount (%) |
| --- | --- | --- |
| 1 | Zinc paraphenol sulfonate | 0.3 |
| 2 | Isopropyl methyl phenol | 0.1 |
| 3 | Ethanol | 5.0 |
| 4 | 1,3-Butylene glycol | 5.0 |
| 5 | Copolymer (3) of present invention | 1.0 |
| 6 | Edetate disodium | 0.01 |
| 7 | 5N Sodium hydroxide | To adjust pH to 8.5 |
| 8 | Polyoxyethylene cetyl ether | 2.0 |
| 9 | Cetanol | 0.5 |
| 10 | Dimethicone | 0.3 |
| 11 | Menthol | 0.1 |
| 12 | Methylparaben | 0.2 |
| 13 | Phenoxyethanol | 0.5 |
| 14 | Fragrance | 0.2 |
| 15 | Purified water | Proportion to make total of 100.0 |

The deodorant gel obtained in Example 38 had a shape without dripping. In addition, acrylic acid ester (A)/compound (B) copolymer of the present invention did not aggregate.

Example 39

Preparation of Color Treatment Using Acrylic Acid Ester (A)/Compound (B) Copolymer (3) of the Present Invention Components 2 to 9 and 11; and a part of Component 1, Components 10, and 13 to 31 were stirred and mixed at respective proportions, and heated to 90° C. Next, the both were mixed at 90° C. and cooled to 60° C. Next, Component 12 was added, further cooled to 45° C., and, finally, Components 1 and 32 were added to prepare a color treatment. Names of the respective components and proportions (% by weight) thereof in Example 39 are shown in Table 22.

TABLE 22

| Component No. | Component | Blending amount (%) |
| --- | --- | --- |
| 1 | Water | Proportion to make total of 100.0 |
| 2 | Cetanol | 4.0 |
| 3 | Glycerin | 3.0 |
| 4 | Castor oil | 2.0 |
| 5 | Dimethicone | 2.0 |
| 6 | Octyldodecanol | 1.0 |
| 7 | Lanolin | 1.0 |
| 8 | Steartrimonium chloride | 1.5 |
| 9 | Behen trimonium chloride | 0.5 |
| 10 | Copolymer (3) of present invention | 1.0 |
| 11 | Amodirnethicone | 0.5 |
| 12 | Arginine | To adjust pH to 8.0 |
| 13 | Sodium pyrrolidone carboxylate | 0.1 |
| 14 | Sodium lactate | 0.1 |
| 15 | Aspartic acid | 0.1 |
| 16 | Pyrrolidone carboxylic acid | 0.05 |
| 17 | Glycine | 0.1 |
| 18 | Methylparaben | 0.2 |
| 19 | Propyl paraben | 0.1 |
| 20 | Gardenia yellow | 0.2 |
| 21 | HC Red 3 | 0.02 |
| 22 | HC Blue 2 | 0.02 |
| 23 | HC Yellow 2 | 0.02 |
| 24 | Basic Blue 75 | 0.1 |
| 25 | Basic Blue 99 | 0.1 |
| 26 | Basic Yellow 57 | 0.1 |
| 27 | Basic Red 51 | 0.1 |
| 28 | Basic Red 76 | 0.05 |
| 29 | Basic Purple 10 | 0.05 |
| 30 | Basic Brown 16 | 0.03 |
| 31 | Basic Brown 17 | 0.03 |
| 32 | Fragrance | 0.2 |

The color treatment obtained in Example 39 had a shape without dripping. In addition, acrylic acid ester (A)/compound (B) copolymer of the present invention did not aggregate.

Example 40

Preparation of Amino Acid-Based Shampoo Using Acrylic Acid Ester (A)/Compound (B) Copolymer (3) of the Present Invention Components 3 to 10 were mixed at respective proportions, heated to 80° C., and a part of Component 1, and Components 2, 12 to 17, and 19 to 23, which had been uniformly mixed beforehand, were slowly added and stirred until they became uniform. Next, the mixture was cooled to 60° C. Then, a viscosity was adjusted with Component 18 by setting the pH to 8.0, and cooled to 30° C. while stirring. Then, Component 11 was further added. Finally, Components 1 and 24 were added to prepare an amino acid-based shampoo. Names of the respective components and proportions (% by weight) thereof in Example 40 are shown in Table 23.

TABLE 23

| Component No. | Component | Blending amount (%) |
| --- | --- | --- |
| 1 | Water | Proportion to make total of 100.0 |
| 2 | Glycerin | 5.0 |
| 3 | Cocamidopropyl betaine | 3.0 |
| 4 | Sodium cocoyl methyl taurine | 2.5 |
| 5 | Sodium lauroyl methy lalanine | 2.5 |
| 6 | Lauramidopropyl betaine | 2.0 |
| 7 | Sodium lauroyl sarcosinate | 2.0 |
| 8 | Sodium laureth-4 carboxylate | 1.0 |
| 9 | Sodium cocoyl glutamate | 1.0 |
| 10 | Decyl glucoside | 1.0 |
| 11 | Sodium chloride | 1.0 |
| 12 | Copolymer (3) of present invention | 1.0 |
| 13 | Dipotassium glycyrrhizinate | 0.2 |
| 14 | Sugarcane extract | 0.01 |
| 15 | Ceramide 2 | 0.02 |

TABLE 23-continued

| Component No. | Component | Blending amount (%) |
|---|---|---|
| 16 | Hydrolyzed hyaluronic acid | 0.02 |
| 17 | Hydrolyzed collagen | 0.01 |
| 18 | 5N Sodium hydroxide | To adjust pH to 8.0 |
| 19 | Citric acid | 0.05 |
| 20 | Polyquaternium-10 | 0.5 |
| 21 | Ethylenediamine disodium tetraacetate | 0.01 |
| 22 | Methylisothiazolinone | 0.0003 |
| 23 | Methylchloroisothiazolinone | 0.001 |
| 24 | Fragrance | 0.3 |

The amino acid-based shampoo obtained in Example 40 had a shape without dripping. In addition, acrylic acid ester (A)/compound (B) copolymer of the present invention did not aggregate.

Example 41

Preparation of Sulfite-Based Shampoo Using Acrylic Acid Ester (A)/Compound (B) Copolymer (3) of the Present Invention Components 2 to 4 and 7 were mixed at respective proportions, heated to 80° C., and a part of Component 1, and Components 5, 8, and 10 to 14, which had been uniformly mixed beforehand, were slowly added and stirred until they became uniform. Next, a viscosity was adjusted with Component 9 by setting the pH to 8.0, and cooled to 30° C. while stirring. Then, Component 6 was further added. Finally, Components 1 and 15 were added to prepare a sulfite-based shampoo. Names of the respective components and proportions (% by weight) thereof in Example 41 are shown in Table 24.

TABLE 24

| Component No. | Component | Blending amount (%) |
|---|---|---|
| 1 | Water | Proportion to make total of 100.0 |
| 2 | Sodium laureth sulfate | 9.0 |
| 3 | Cocamidopropyl betaine | 6.0 |
| 4 | Cocamidomethyl monoethanolamine | 2.0 |
| 5 | Polyquaternium-10 | 2.5 |
| 6 | Sodium chloride | 1.0 |
| 7 | Dimethicone | 0.1 |
| 8 | Copolymer (3) of present invention | 1.0 |
| 9 | 5N Sodium hydroxide | To adjust pH to 8.0 |
| 10 | Citric acid | 0.1 |
| 11 | Hydrolyzed collagen | 0.01 |
| 12 | Ethylenediamine disodium tetraacetate | 0.1 |
| 13 | Methylparaben | 0.1 |
| 14 | Sodium benzoate | 0.05 |
| 15 | Fragrance | 0.3 |

The sulfite-based shampoo obtained in Example 41 had a shape without dripping. In addition, acrylic acid ester (A)/compound (B) copolymer of the present invention did not aggregate.

Example 42

Preparation of Paraphenylenediamine-Based Oxidative Hair Dye Using Acrylic Acid Ester (A)/Compound (B) Copolymer (3) of the Present Invention Components 1 to 5, a part of Component 6, and Components 12, 13, and 15 to 18; and Components 8 to 11 were stirred and mixed at respective proportions, and heated to 90° C. Next, the both were mixed at 90° C. and cooled to 60° C. Next, Component 7 was added, further cooled to 45° C., and, finally, Components 6 and 14 were added to prepare a paraphenylenediamine-based oxidative hair dye. Names of the respective components and proportions (% by weight) thereof in Example 42 are shown in Table 25.

TABLE 25

| Component No. | Component | Blending amount (%) |
|---|---|---|
| 1 | Paraphenylenediamine | 0.30 |
| 2 | Resorcin | 0.05 |
| 3 | 2,4-Diamino phenoxyethanol hydrochloride | 0.10 |
| 4 | α-Naphthol | 0.10 |
| 5 | Metaaminophenol | 0.05 |
| 6 | Water | Proportion to make total of 100.0 |
| 7 | 25% Ammonia water | To adjust pH to 9.0 |
| 8 | Dicetyl phosphate | 2.00 |
| 9 | POE cetyl ether phosphate | 1.50 |
| 10 | POE oleyl ether phosphate | 1.50 |
| 11 | Cetostearyl alcohol | 5.00 |
| 12 | Copolymer (3) of present invention | 1.00 |
| 13 | 1.3-Butylene glycol | 5.00 |
| 14 | Fragrance | 0.20 |
| 15 | L-Ascorbic acid | 0.10 |
| 16 | Sodium sulfite (anhydrous) | 0.10 |
| 17 | Edetate | 0.10 |
| 18 | Trisodium ethylenediamine disuccinate | 0.10 |

The paraphenylenediamine-based oxidative hair dye obtained in Example 42 had a shape without dripping. In addition, acrylic acid ester (A)/compound (B) copolymer of the present invention did not aggregate.

Example 43

Preparation of Toluenediamine-Based Oxidative Hair Dye Using Acrylic Acid Ester (A)/Compound (B) Copolymer (3) of the Present Invention Components 1 to 5, 12 to 20, and a part of Component 24; and Components 6 to 11 were stirred and mixed at respective proportions, and heated to 90° C. Next, the both were mixed at 90° C. and cooled to 60° C. Next, Components 22 and 23 were added, further cooled to 45° C., and, finally, Components 21 and 24 were added to prepare a toluenediamine-based oxidative hair dye. Names of the respective components and proportions (% by weight) thereof in Example 43 are shown in Table 26.

TABLE 26

| Component No. | Component | Blending amount (%) |
|---|---|---|
| 1 | Toluene-2,5-diamine sulfate | 0.20 |
| 2 | Resorcin | 0.12 |
| 3 | 2,4-Diamino phenoxyethanol hydrochloride | 0.02 |
| 4 | Metaaminophenol | 0.04 |
| 5 | 5-Aminoorthocresol | 0.03 |
| 6 | Liquid paraffin | 2.00 |
| 7 | Paraffin | 1.50 |
| 8 | Polyethylene glycol | 1.50 |
| 9 | Cetanol | 3.00 |
| 10 | POE cetyl ether phosphate | 2.70 |
| 11 | Stearyl trimethyl ammonium chloride | 0.02 |
| 12 | Concentrated glycerin | 3.00 |
| 13 | Copolymer (3) of present invention | 1.00 |
| 14 | Xanthan gum | 0.20 |
| 15 | Edetate disodium | 0.20 |
| 16 | Sodium L-ascorbate | 0.30 |
| 17 | Anhydrous sodium sulfite | 0.50 |

TABLE 26-continued

| Component No. | Component | Blending amount (%) |
|---|---|---|
| 18 | L-Arginine | 0.01 |
| 19 | L-Proline | 0.01 |
| 20 | Licorice root extract | 0.05 |
| 21 | Fragrance | 0.30 |
| 22 | Strong ammonia water | To adjust pH to 9.0 |
| 23 | Ammonium carbonate | 1.20 |
| 24 | Purified water | Proportion to make total of 100.0 |

The toluenediamine-based oxidative hair dye obtained in Example 43 had a shape without dripping. In addition, acrylic acid ester (A)/compound (B) copolymer of the present invention did not aggregate.

Example 44

Preparation of Thioglycolic Acid-Based Liquid for Permanent Wave Using Acrylic Acid Ester (A)/Compound (B) Copolymer (3) of the Present Invention Components 1 to 3, and a part of Component 5 were mixed at respective proportions, and a viscosity was adjusted with Components 4 and 5 by setting the pH to 8.5, to form a first liquid. Next, Components 6 to 9 were mixed to prepare a second liquid. Next, the first liquid and the second liquid were mixed at proportions of equal amount to prepare a thioglycolic acid-based liquid for permanent wave. Names of the respective components and proportions (% by weight) thereof in Example 44 are shown in Table 27.

TABLE 27

| Component No. | Component | Blending amount (%) |
|---|---|---|
| | First liquid | |
| 1 | Thioglycolic acid | 6.0 |
| 2 | Monoammonium dihydrogen phosphate | 2.0 |
| 3 | Copolymer (3) of present invention | 1.0 |
| 4 | Ammonia water | To adjust pH to 8.5 |
| 5 | Purified water | Proportion to make 100.0 in first liquid |
| | Second liquid | |
| 6 | Hydrogen peroxide | 6.0 |
| 7 | Monoammonium dihydrogen phosphate | Adequate amount |
| 8 | Phosphoric acid | Adequate amount to adjust pH to 6.5 |
| 9 | Purified water | Proportion to make 100.0 in second liquid |

The thioglycolic acid-based liquid for permanent wave obtained in Example 44 had a shape without dripping. In addition, acrylic acid ester (A)/compound (B) copolymer of the present invention did not aggregate.

Example 45

Preparation of Cysteamine-Based Curling Preparation Using Acrylic Acid Ester (A)/Compound (B) Copolymer (3) of the Present Invention Components 1 to 3, and a part of Component 5 were mixed at respective proportions, and a viscosity was adjusted with Components 4 and 5 by setting the pH to 9.0, to form a first liquid. Next, Components 6 to 9 were mixed to prepare a second liquid. Next, the first liquid and the second liquid were mixed at proportions of equal amount to prepare a cysteamine-based curling preparation. Names of the respective components and proportions (% by weight) thereof in Example 45 are shown in Table 28.

TABLE 28

| Component No. | Component | Blending amount (%) |
|---|---|---|
| | First liquid | |
| 1 | L-Cysteamine | 5.0 |
| 2 | Monoammonium dihydrogen phosphate | 2.0 |
| 3 | Copolymer (3) of present invention | 1.0 |
| 4 | Ammonia water | To adjust pH to 9.0 |
| 5 | Purified water | Proportion to make 100.0 in first liquid |
| | Second liquid | |
| 6 | Sodium bromate | 6.0 |
| 7 | Monoammonium dihydrogen phosphate | Adequate amount |
| 8 | Phosphoric acid | Adequate amount to adjust pH to 6.0 |
| 9 | Purified water | Proportion to make 100.0 in second liquid |

The cysteamine-based curling preparation obtained in Example 45 had a shape without dripping. In addition, acrylic acid ester (A)/compound (B) copolymer of the present invention did not aggregate.

As is clearly shown from Examples 21 to 45, in various cosmetic preparations using acrylic acid ester (A)/compound (B) copolymer of the present invention, acrylic acid ester (A)/compound (B) copolymer of the present invention did not aggregate, and had a shape without dripping.

INDUSTRIAL APPLICABILITY

Since acrylic acid ester (A)/compound (B) copolymer of the present invention can be used as a thickening agent having excellent characteristics, it is possible to provide various cosmetic preparations, such as a skin lotion, an emulsion, a beauty liquid, a cream, a cleansing cream, a cleansing gel, a styling gel, an eyeliner, mascara, a foundation, and a body shampoo, which have excellent feeling in use and applying properties as well as a unique tactile feeling.

The invention claimed is:

1. An acrylic acid ester (A)/compound (B)/compound (C) copolymer, comprising, as constitutional components: an acrylic acid ester (A); a compound (B); and a compound (C), wherein the acrylic acid ester (A) is represented by a general formula [1]:

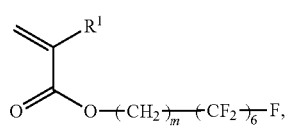

[1]

wherein $R^1$ represents a hydrogen atom or an alkyl group having 1 to 6 carbon atoms, and m represents an integer of 2 to 4, the compound (B) has, in each molecule, a polymerizable unsaturated group and a functional group selected from the group consisting of a carboxyl group, a sulfo group, and a phosphate group, and the compound (C) is a crosslinking agent, a weight ratio of the acrylic acid ester (A) and the compound (B), which is (A)/(B), is 9.0/91.0 to 28.5/71.5, the acrylic acid ester (A)/compound (B)/compound (C) copolymer has a following characteristic (1):
(1) an aqueous solution containing 1% by weight of the acrylic acid ester (A)/compound (B)/compound (C) copolymer and 3% by weight of ascorbyl magnesium phosphate and having a pH of 8 has a viscosity of 5,000 mPa·s or more at 20° C., and the compound (B) is a compound represented by any one of general formulae [2], [4] and [5]:

general formula [2]:

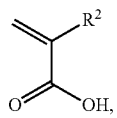

[2]

wherein $R_2$ represents a hydrogen atom or an alkyl group having 1 to 6 carbon atoms;

general formula [4]:

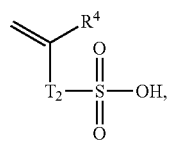

[4]

wherein $T_2$ represents a bond or an alkylene group having 1 to 6 carbon atoms, and $R_4$ represents a hydrogen atom or an alkyl group having 1 to 6 carbon atoms; and general formula [5]:

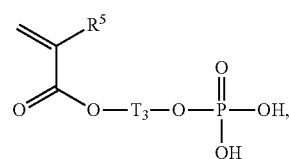

[5]

wherein $T_3$ represents an alkylene group having 1 to 6 carbon atoms, and $R_5$ represents a hydrogen atom or an alkyl group having 1 to 6 carbon atoms.

2. The copolymer according to claim 1, wherein the weight ratio of the acrylic acid ester (A) and the compound (B), which is (A)/(B), is 14.0/86.0 to 27.3/72.7.

3. The copolymer according to claim 1, wherein the weight ratio of the acrylic acid ester (A) and the compound (B), which is (A)/(B), is 14.0/86.0 to 25.0/75.0.

4. The copolymer according to claim 1, wherein a proportion of the compound (C) is 0.0001 to 1.5 parts by weight with respect to a total of the acrylic acid ester (A) and the compound (B) which is 100 parts by weight.

5. The copolymer according to claim 1, wherein the acrylic acid ester (A) is 2-perfluorohexylethyl (meth)acrylate.

6. The copolymer according to claim 1, wherein the compound (B) is a compound represented by the general formula [2], general formula [2]:

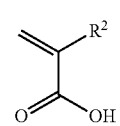

[2]

wherein $R^2$ represents a hydrogen atom or an alkyl group having 1 to 6 carbon atoms.

7. The copolymer according to claim 1, wherein the compound (C) is a compound represented by a general formula [7], a compound represented by a general formula [8], a compound represented by a general formula [9], or a compound represented by a general formula [16]:

general formula [7]:

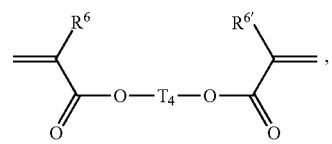

[7]

wherein $T_4$ represents an alkylene group having 1 to 20 carbon atoms, a group represented by a general formula [7-1], or a group represented by a general formula [7-2], and $R^6$ and $R^{6'}$ each independently represents a hydrogen atom or a methyl group;

general formula [7-1]:

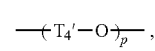

[7-1]

wherein p pieces of $T_4'$ each independently represents an alkylene group having 1 to 6 carbon atoms, and p represents an integer of 1 to 6;

general formula [7-2]:

[7-2]

wherein p' pieces of $T_4''$ and $T_4'''$ each independently represents an alkylene group having 1 to 6 carbon atoms, and p' represents an integer of 1 to 12;

general formula [8]:

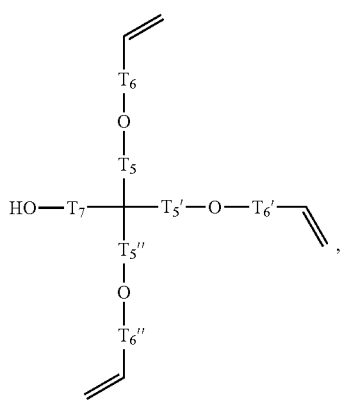

wherein $T_5$, $T_5'$, $T_5''$, $T_6$, $T_6'$, $T_6''$, and $T_7$ each independently represents an alkylene group having 1 to 3 carbon atoms;

general formula [9]:

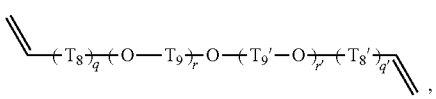

wherein q pieces of $T_8$, q' pieces of $T_8'$, r pieces of $T_9$, and r' pieces of $T_9'$ each independently represents an alkylene group having 1 to 6 carbon atoms, q and q' represent 0 or 1, r represents an integer of 1 to 6, and r' represents an integer of 0 to 6; and general formula [16]:

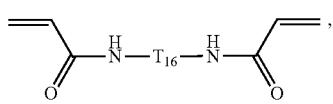

wherein $T_{16}$ represents an alkylene group having 1 to 6 carbon atoms.

8. The copolymer according to claim 1, wherein the compound (C) is 1,10-decanediol diacrylate, pentaerythritol triallyl ether, diethylene glycol diallyl ether, or N,N'-methylenebisacrylamide.

9. The copolymer according to claim 1, wherein the compound (C) is diethylene glycol diallyl ether.

10. A cosmetic preparation comprising an acrylic acid ester (A)/compound (B)/compound (C) copolymer, comprising, as constitutional components: an acrylic acid ester (A); a compound (B); and a compound (C), wherein the acrylic acid ester (A) is represented by a general formula [1]:

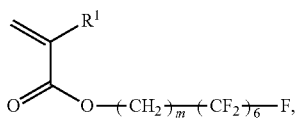

wherein R1 represents a hydrogen atom or an alkyl group having 1 to 6 carbon atoms, and m represents an integer of 2 to 4, the compound (B) has, in each molecule, a polymerizable unsaturated group and any functional group selected from the group consisting of a carboxyl group, a sulfo group, and a phosphate group, and the compound (C) is a crosslinking agent, a weight ratio of the acrylic acid ester (A) and the compound (B), which is (A)/(B), is 9.0/91.0 to 28.5/71.5, and the compound (B) is a compound represented by any one of the general formulae [2], [4] and 5:

general formula [2]:

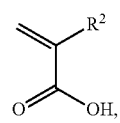

wherein $R_2$ represents a hydrogen atom or an alkyl group having 1 to 6 carbon atoms;

general formula [4]:

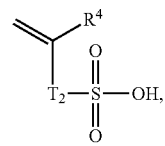

wherein $T_2$ represents a bond or an alkylene group having 1 to 6 carbon atoms, and $R_4$ represents a hydrogen atom or an alkyl group having 1 to 6 carbon atoms; and general formula [5]:

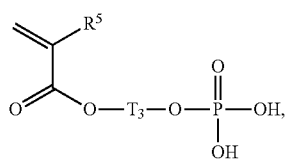

wherein T3 represents an alkylene group having 1 to 6 carbon atoms, and R5 represents a hydrogen atom or an alkyl group having 1 to 6 carbon atoms.

11. The cosmetic preparation according to claim 10, wherein further comprising an electrolyte.

12. The cosmetic preparation according to claim 11, wherein the electrolyte is a polyvalent electrolyte.

13. A thickening agent comprising an acrylic acid ester (A)/compound (B)/compound (C) copolymer, comprising, as constitutional components: an acrylic acid ester (A); a compound (B), and a compound (C), and a polyvalent electrolyte, wherein the acrylic acid ester (A) is represented by a general formula [1]:

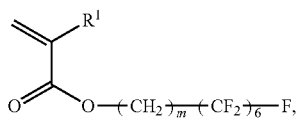

[1]

wherein $R_1$ represents a hydrogen atom or an alkyl group having 1 to 6 carbon atoms, and m represents an integer of 2 to 4, the compound (B) has, in each molecule, a polymerizable unsaturated group and any functional group selected from the group consisting of a carboxyl group, a sulfo group, and a phosphate group, and the compound (C) is a crosslinking agent, a weight ratio of the acrylic acid ester (A) and the compound (B), which is (A)/(B), is 9.0/91.0 to 28.5/71.5, and a blending amount of the polyvalent electrolyte is 1 to 3,000 parts by weight with respect to 100 parts by weight of the acrylic acid ester (A)/compound (B)/compound (C) copolymer, and the compound (B) is a compound represented by any one of general formulae [2], [4] and [5];

general formula [2]:

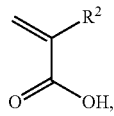

[2]

wherein $R_2$ represents a hydrogen atom or an alkyl group having 1 to 6 carbon atoms;

general formula [4]:

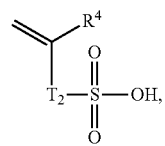

[4]

wherein $T_2$ represents a bond or an alkylene group having 1 to 6 carbon atoms, and $R_4$ represents a hydrogen atom or an alkyl group having 1 to 6 carbon atoms; and general formula [5]:

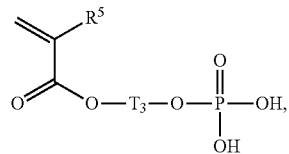

[5]

wherein $T_3$ represents an alkylene group having 1 to 6 carbon atoms, and $R_5$ represents a hydrogen atom or an alkyl group having 1 to 6 carbon atoms.

14. The cosmetic preparation according to claim 11, wherein a blending amount of the electrolyte is 1 to 3,000 parts by weight with respect to 100 parts by weight of the acrylic acid ester (A)/compound (B)/compound (C) copolymer.

* * * * *